US008822482B2

(12) United States Patent
Wang et al.

(10) Patent No.: US 8,822,482 B2
(45) Date of Patent: Sep. 2, 2014

(54) ICOTINIB HYDROCHLORIDE, SYNTHESIS, CRYSTALLINE FORMS, PHARMACEUTICAL COMPOSITIONS, AND USES THEREOF

(75) Inventors: Yinxiang Wang, Cheshire, CT (US); Guojian Xie, Cheshire, CT (US); Lieming Ding, Hangzhou (CN); Fenlai Tan, Troy, MI (US); Yunyan Hu, Beijing (CN); Wei He, Beijing (CN); Bin Han, Beijing (CN); Wei Long, Beijing (CN); Yong Liu, Beijing (CN); Haima Ai, Beijing (CN); Charles Davis, Germantown, WI (US); Don Zhang, Branford, CT (US)

(73) Assignee: Beta Pharma, Inc., Branford, CT (US)

( * ) Notice: Subject to any disclaimer, the term of this patent is extended or adjusted under 35 U.S.C. 154(b) by 649 days.

(21) Appl. No.: 13/003,216

(22) PCT Filed: Jul. 7, 2009

(86) PCT No.: PCT/CN2009/000773
§ 371 (c)(1),
(2), (4) Date: Apr. 14, 2011

(87) PCT Pub. No.: WO2010/003313
PCT Pub. Date: Jan. 14, 2010

(65) Prior Publication Data
US 2011/0182882 A1    Jul. 28, 2011

(30) Foreign Application Priority Data

Jul. 8, 2008   (CN) .......................... 2008 1 0132631
Jul. 17, 2008  (CN) .......................... 2008 1 0132458
Dec. 23, 2008  (CN) .......................... 2008 1 0188272

(51) Int. Cl.
*A61K 31/519* (2006.01)
*C07D 491/056* (2006.01)
(52) U.S. Cl.
CPC ........... *C07D 491/056* (2013.01); *A61K 31/519* (2013.01)
USPC .......................................... 514/267; 544/250
(58) Field of Classification Search
CPC ........................... A61K 31/519; C07D 491/056
USPC .......................................... 514/267; 544/250
See application file for complete search history.

(56) References Cited

FOREIGN PATENT DOCUMENTS

CN      1534026 A       10/2004
JP      2002338577 A    11/2002
WO      WO 03/082830  * 10/2003  ........... C07D 239/86

OTHER PUBLICATIONS

Yakshin, et al., Macrocyclic Effect in Extraction of Metals by Crown Compounds Containing Diphenyloxy Spacers, Doklady Physical Chemistry, Part 2, 280-284 (May 30, 2007).*
Gibson, et al., Regioselective routes to disubstituted dibenzo crown ethers and their complexations, Org. Biomol. Chem., 3, 2114-2121 (2005).*
Berge, et al., Pharmaceutical Salts, J. of Pharm. Sciences (1977).*
Alcock, Nathaniel W., et al., "Transition-Metal complexes of superstructured cyclidene macrobicycles: Structural features and their chemical consequences.3. Cyclidenes with long polymethylene bridges," Inorganic Chemistry vol. 29, pp. 2599-2607, (1990).
Calderon, Veronica, et al., "Synthesis and characterization of new aromatic polyamides bearing crown ethers or their dipodal counterparts in the pendant structure.1. Benzo-12-crown-4 and ortho-Bis(2-ethoxyethoxy) benzene," Journal of Polymer Science, vol. 44, No. 7, pp. 2270-2281, (2006).
Guan, Zhongmin, et al., "Metabolite identification of a new antitumor agent icotinib in rats using liquid chromatography/tandem mass spectrometry," Rapid Communications in Mass Spectrometry, vol. 22, No. 14, pp. 2176-2184, (2008).
Yand, Cailing, et al., "Effect of icotinib on human tongue carcinoma a cell line Tca8113 proliferation," Journal of Zhengzhou University (Medical Sciences), vol. 43, No. 4, pp. 701-703, (2008).
Keegstra, Erik M.D., et al., "A highly selective synthesis of monodisperse oligo (ethylene glycols)," Journal of Organic Chemistry, vol. 57, pp. 6678-6680, (1992).
The International Search Report for PCT/CN2009/000773, date completed Sep. 24, 2009, date mailed Oct. 15, 2009.
"Setting of specifications and test methods for new drugs," Notification of the Ministry of Health, Labor and welfare, Durg Evaluation and Licensing Division No. 568 (2001) (English translation of pertinent sections).

* cited by examiner

*Primary Examiner* — Erich A Leeser
(74) *Attorney, Agent, or Firm* — Fox Rothschild LLP; Wansheng Jerry Liu

(57) ABSTRACT

The invention relates to 4-[(3-ethynylphenyl)amino]-6,7-benzo-12-crown-quinazoline hydrochloride, its new crystalline forms, its therapeutic usage for treatment of diseases mediated by EGFR kinase and its combinatory therapeutic usage together with other therapeutic agents. The invention also provides synthetic methods for preparation of 4-[(3-ethynylphenyl)amino]-6,7-benzo-12-crown-quinazoline hydrochloride, its new crystalline forms, and the relevant synthetic intermediates for synthesis of 4-[(3-ethynylphenyl) amino]-6,7-benzo-12-crown-quinazoline hydrochloride.

35 Claims, 10 Drawing Sheets

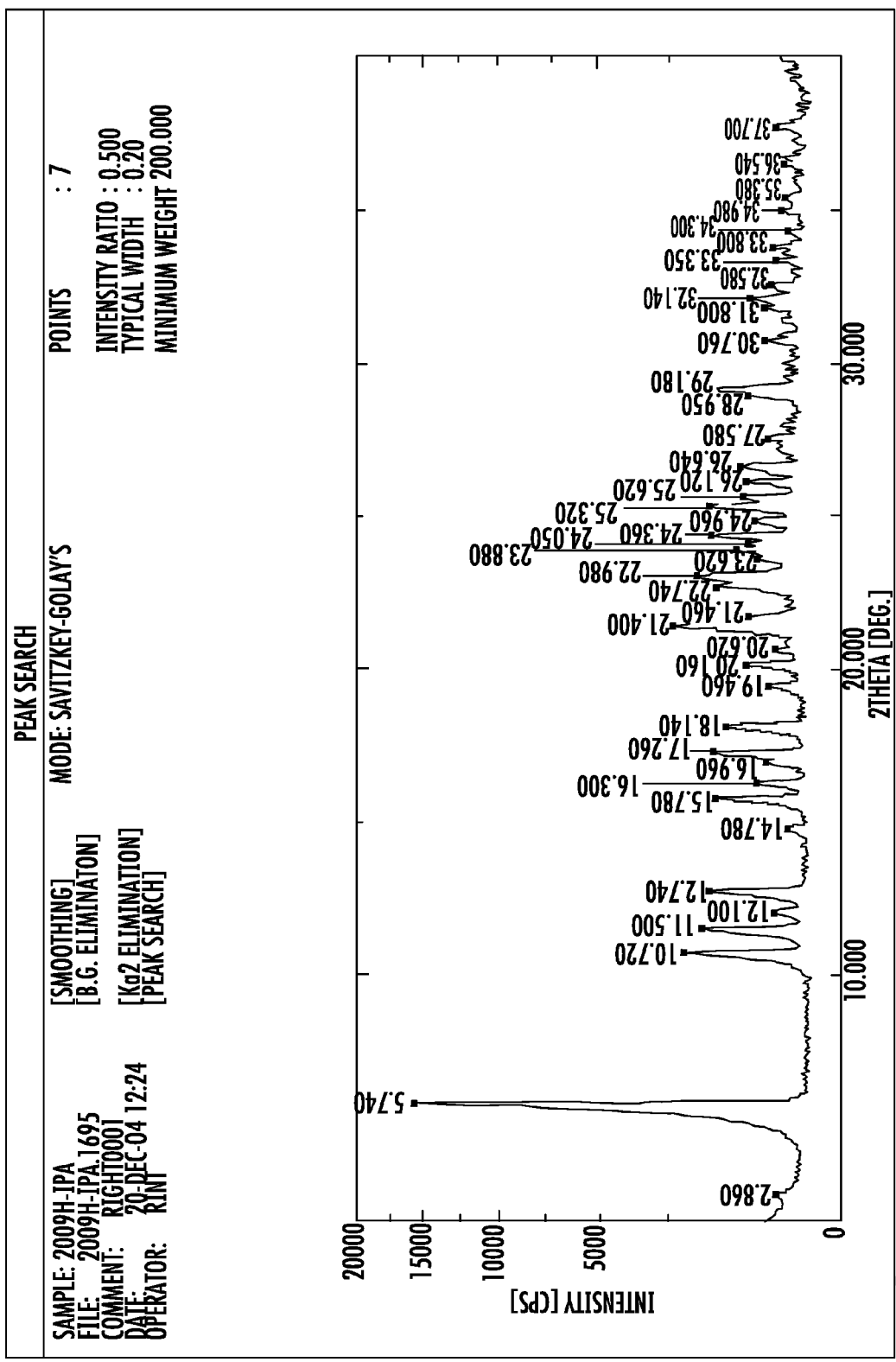
FIG. 1 X-RAY DIFFRACTION PATTERN OF ICOTINIB HYDROCHLORIDE CRYSTALLINE FORM I (CRYSTALLIZATION FROM ISOPROPANOL)

| | | | PEAK SEARCH | | | |
|---|---|---|---|---|---|---|
| SAMPLE: | 2009H-IPA | | FILE: | 2009H-IPA.1695 | COMMENT: RIGHT0001 | |
| DATE: | 20-DEC-04 12:24 | | OPERATOR: | AINT | | |

| PEAK NO. | 2THETA | FWHM | D-VALUE | INTENSITY | I/I0 | PEAK No. | 2THETA | FWHM | D-VALUE | INTENSITY | I/I0 |
|---|---|---|---|---|---|---|---|---|---|---|---|
| 1 | 2.860 | ***** | 30.8660 | 354 | 2 | 31 | 29.180 | 0.165 | 3.0579 | 1266 | 8 |
| 2 | 5.740 | 0.165 | 15.3841 | 15680 | 100 | 32 | 30.760 | 0.118 | 2.9043 | 473 | 3 |
| 3 | 10.720 | 0.165 | 8.2459 | 2088 | 13 | 33 | 31.800 | 0.141 | 2.8117 | 528 | 3 |
| 4 | 11.500 | 0.165 | 7.6884 | 1648 | 10 | 34 | 32.140 | 0.259 | 2.7827 | 761 | 5 |
| 5 | 12.100 | 0.165 | 7.3084 | 408 | 3 | 35 | 32.580 | 0.141 | 2.7461 | 411 | 3 |
| 6 | 12.740 | 0.165 | 5.9427 | 1404 | 9 | 36 | 33.360 | ***** | 2.6837 | 366 | 2 |
| 7 | 14.780 | ***** | 5.9887 | 259 | 2 | 37 | 33.800 | 0.141 | 2.8497 | 382 | 2 |
| 8 | 15.780 | 0.188 | 5.6114 | 1286 | 8 | 38 | 34.300 | ***** | 2.6122 | 239 | 2 |
| 9 | 16.300 | 0.141 | 5.4335 | 599 | 4 | 39 | 34.980 | ***** | 2.5630 | 303 | 2 |
| 10 | 16.960 | 0.165 | 5.2235 | 457 | 3 | 40 | 35.380 | ***** | 2.5349 | 281 | 2 |
| 11 | 17.260 | 0.188 | 5.1334 | 1423 | 9 | 41 | 36.540 | ***** | 2.4571 | 297 | 2 |
| 12 | 18.140 | 0.259 | 4.8863 | 1066 | 7 | 42 | 37.700 | ***** | 2.3841 | 368 | 2 |
| 13 | 19.450 | 0.188 | 4.5577 | 432 | 3 | | | | | | |
| 14 | 20.180 | 0.165 | 4.4010 | 812 | 5 | | | | | | |
| 15 | 20.520 | 0.185 | 4.3039 | 345 | 2 | | | | | | |
| 16 | 21.400 | 0.188 | 4.1487 | 2526 | 17 | | | | | | |
| 17 | 21.660 | 0.141 | 4.0995 | 833 | 5 | | | | | | |
| 18 | 22.740 | 0.118 | 3.9072 | 1213 | 8 | | | | | | |
| 19 | 22.980 | 0.118 | 3.8669 | 1958 | 12 | | | | | | |
| 20 | 23.620 | 0.118 | 3.7636 | 635 | 4 | | | | | | |
| 21 | 23.880 | 0.141 | 3.7232 | 905 | 6 | | | | | | |
| 22 | 24.120 | 0.116 | 3.6927 | 790 | 5 | | | | | | |
| 23 | 24.360 | 0.165 | 3.6509 | 1415 | 9 | | | | | | |
| 24 | 24.880 | 0.259 | 3.5786 | 662 | 4 | | | | | | |
| 25 | 25.320 | 0.188 | 3.5145 | 1464 | 9 | | | | | | |
| 26 | 25.620 | 0.212 | 3.4741 | 876 | 6 | | | | | | |
| 27 | 26.120 | 0.188 | 3.4088 | 736 | 5 | | | | | | |
| 28 | 26.640 | 0.282 | 3.3434 | 870 | 5 | | | | | | |
| 29 | 27.580 | 0.212 | 3.2315 | 463 | 3 | | | | | | |
| 30 | 28.960 | 0.118 | 3.0806 | 713 | 4 | | | | | | |

FIG. 1 CONT. X-RAY DIFFRACTION PATTERN OF LCOTINIB HYDROCHLORIDE CRYSTALLINE FORM I (CRYSTALLIZATIONL FROM ISOPROPANOL)

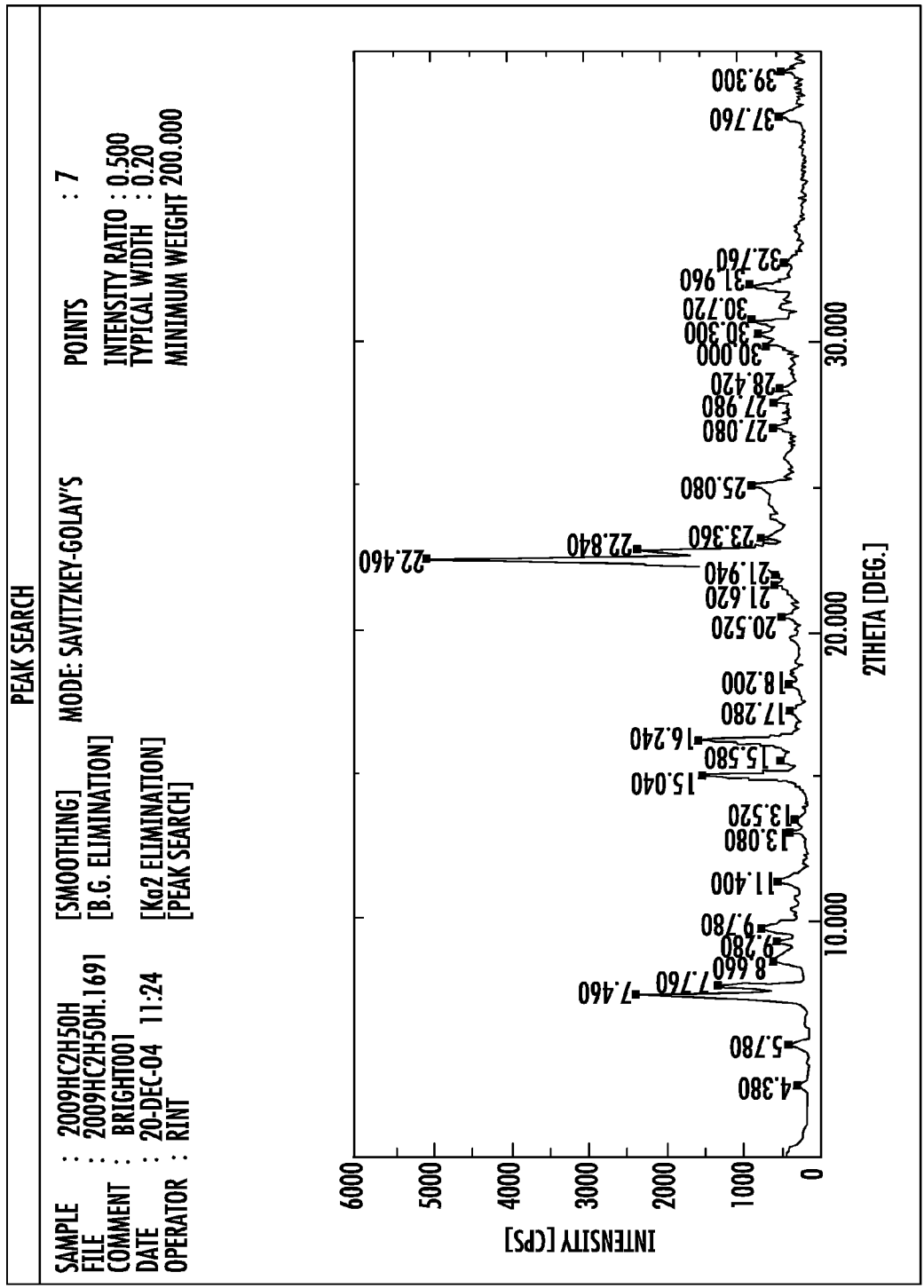
FIG. 2 X-RAY DIFFRACTION PATTERN OF ICOTINIB HYDROCHLORIDE CRYSTALLINE FORM II (CRYSTALLIZATION FROM 50% ETHANOL)

PEAK SEARCH

| SAMPLE | : 2009HC2H5OH | | FILE | : 2009HC2H5OH.1691 | | COMMENT | : RIGHT 0001 | | | |
|---|---|---|---|---|---|---|---|---|---|---|
| DATE | : 20-DEC-04 11:42 | | OPERATOR | :RINT | | | | | | |
| PEAK NO. | 2THETA | FWHM | D-VALUE | INTENSITY | I/IO | PEAK No. | 2THETA | FWHM | D-VALUE | INTENSITY | I/IO |
| 1 | 4.380 | ***** | 20.1574 | 291 | 6 | 31 | 37.760 | 0.118 | 2.3804 | 457 | 9 |
| 2 | 5.780 | ***** | 15.2777 | 425 | 8 | 32 | 39.300 | 0.118 | 2.2906 | 426 | 8 |
| 3 | 7.460 | 0.235 | 11.8405 | 2336 | 46 | | | | | | |
| 4 | 7.760 | 0.165 | 11.3834 | 1359 | 27 | | | | | | |
| 5 | 8.660 | 0.141 | 10.2023 | 618 | 12 | | | | | | |
| 6 | 9.280 | 0.141 | 9.5220 | 560 | 11 | | | | | | |
| 7 | 9.780 | 0.282 | 9.0363 | 795 | 16 | | | | | | |
| 8 | 11.400 | 0.212 | 7.7556 | 544 | 11 | | | | | | |
| 9 | 13.080 | ***** | 6.7630 | 370 | 7 | | | | | | |
| 10 | 13.520 | ***** | 6.5438 | 303 | 6 | | | | | | |
| 11 | 15.040 | 0.212 | 5.8857 | 1507 | 30 | | | | | | |
| 12 | 15.580 | 0.118 | 5.6829 | 480 | 9 | | | | | | |
| 13 | 16.240 | 0.212 | 5.4534 | 1556 | 31 | | | | | | |
| 14 | 17.280 | ***** | 5.1275 | 357 | 7 | | | | | | |
| 15 | 18.200 | ***** | 4.6703 | 354 | 7 | | | | | | |
| 16 | 20.520 | 0.141 | 4.3246 | 475 | 9 | | | | | | |
| 17 | 21.620 | 0.116 | 4.1070 | 501 | 10 | | | | | | |
| 18 | 21.840 | 0.118 | 4.0478 | 497 | 10 | | | | | | |
| 19 | 22.460 | 0.259 | 3.9553 | 5054 | 100 | | | | | | |
| 20 | 22.840 | 0.141 | 3.8903 | 2359 | 47 | | | | | | |
| 21 | 23.360 | 0.141 | 3.8049 | 585 | 12 | | | | | | |
| 22 | 25.080 | 0.141 | 3.5477 | 885 | 10 | | | | | | |
| 23 | 27.080 | 0.118 | 3.2901 | 515 | 10 | | | | | | |
| 24 | 27.980 | 0.165 | 3.1862 | 519 | 9 | | | | | | |
| 25 | 28.420 | 0.118 | 3.1379 | 447 | 9 | | | | | | |
| 26 | 30.000 | 0.186 | 2.9761 | 626 | 12 | | | | | | |
| 27 | 30.300 | 0.141 | 2.9474 | 762 | 15 | | | | | | |
| 28 | 30.720 | 0.212 | 2.9080 | 815 | 16 | | | | | | |
| 29 | 31.960 | 0.188 | 2.7980 | 871 | 17 | | | | | | |
| 30 | 32.760 | 0.165 | 2.7314 | 383 | 8 | | | | | | |

FIG. 2 CONT. X-RAY DIFFRACTION PATTERN OF ICOTINIB HYDROCHLORIDE CRYSTALLINE FORM II (CRYSTALLIZATION FROM 50% ETHANOL)

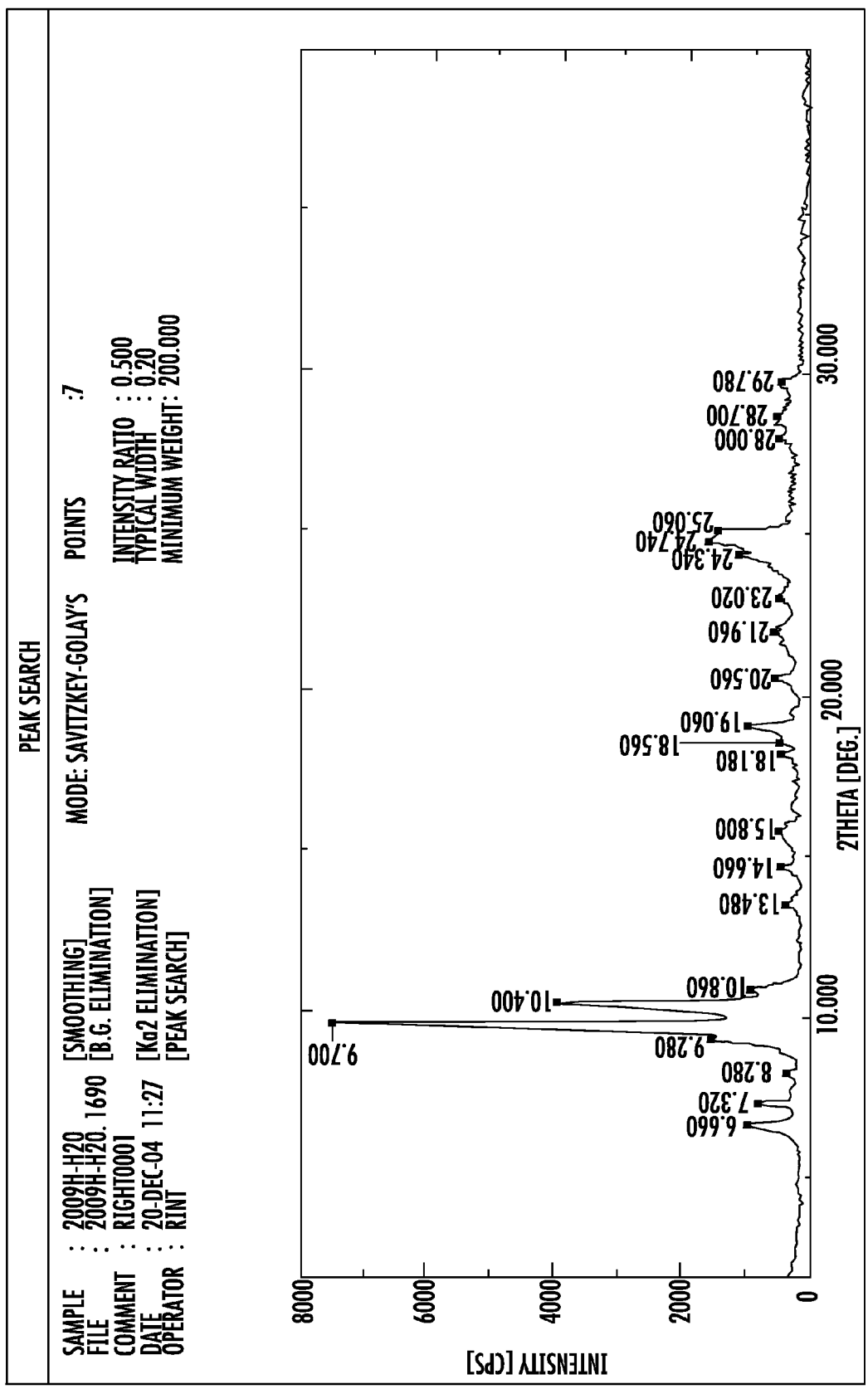
FIG. 3 X-RAY DIFFRACTION PATTERN OF ICOTINIB HYDROCHLORIDE CRYSTALLINE FORM III (CRYSTALLIZATION FROM AQUEOUS SOLVENT)

PEAK SEARCH

| SAMPLE | : 2009H-H2C | | FILE | : 2009H-H20: 1690 | | COMMENT | : RIGHT001 | |
|---|---|---|---|---|---|---|---|---|
| DATE | : 20-DEC-04 11:27 | | OPERATOR | :RINT | | | | |

| PEAK NO. | 2THETA | FWHM | D-VALUE | INTENSITY | I/I0 | PEAK No. | 2THETA | FWHM | D-VALUE | INTENSITY | I/I0 |
|---|---|---|---|---|---|---|---|---|---|---|---|
| 1 | 6.660 | 0.282 | 13.2609 | 1019 | 14 | | | | | | |
| 2 | 7.320 | 0.165 | 12.0656 | 838 | 11 | | | | | | |
| 3 | 8.280 | ***** | 10.6696 | 380 | 5 | | | | | | |
| 4 | 9.280 | 0.165 | 9.5220 | 1575 | 21 | | | | | | |
| 5 | 9.720 | 0.188 | 9.0919 | 7527 | 100 | | | | | | |
| 6 | 10.400 | 0.235 | 8.4989 | 3976 | 53 | | | | | | |
| 7 | 10.860 | 0.188 | 8.1400 | 968 | 13 | | | | | | |
| 8 | 13.480 | ***** | 6.5632 | 425 | 6 | | | | | | |
| 9 | 14.650 | 0.165 | 6.0374 | 514 | 7 | | | | | | |
| 10 | 15.800 | 0.165 | 5.6043 | 537 | 7 | | | | | | |
| 11 | 18.180 | 0.188 | 4.8756 | 541 | 7 | | | | | | |
| 12 | 18.560 | 0.141 | 4.7767 | 544 | 7 | | | | | | |
| 13 | 19.060 | 0.212 | 4.6525 | 1065 | 14 | | | | | | |
| 14 | 20.560 | 0.188 | 4.3163 | 625 | 8 | | | | | | |
| 15 | 21.960 | ***** | 4.0442 | 652 | 9 | | | | | | |
| 16 | 23.020 | ***** | 3.8603 | 593 | 8 | | | | | | |
| 17 | 24.340 | 0.118 | 3.6539 | 1213 | 16 | | | | | | |
| 18 | 24.740 | 0.212 | 3.5957 | 1709 | 23 | | | | | | |
| 19 | 25.060 | 0.212 | 3.5505 | 1547 | 21 | | | | | | |
| 20 | 28.000 | 0.141 | 3.1840 | 563 | 8 | | | | | | |
| 21 | 28.700 | 0.141 | 3.1079 | 613 | 8 | | | | | | |
| 22 | 29.780 | 0.141 | 2.9976 | 579 | 8 | | | | | | |

FIG. 3 CONT. X-RAY DIFFRACTION PATTERN OF ICOTINIB HYDROCHLORIDE CRYSTALLINE FORM III (CRYSTALLIZATION FROM AQUEOUS SOLVENT)

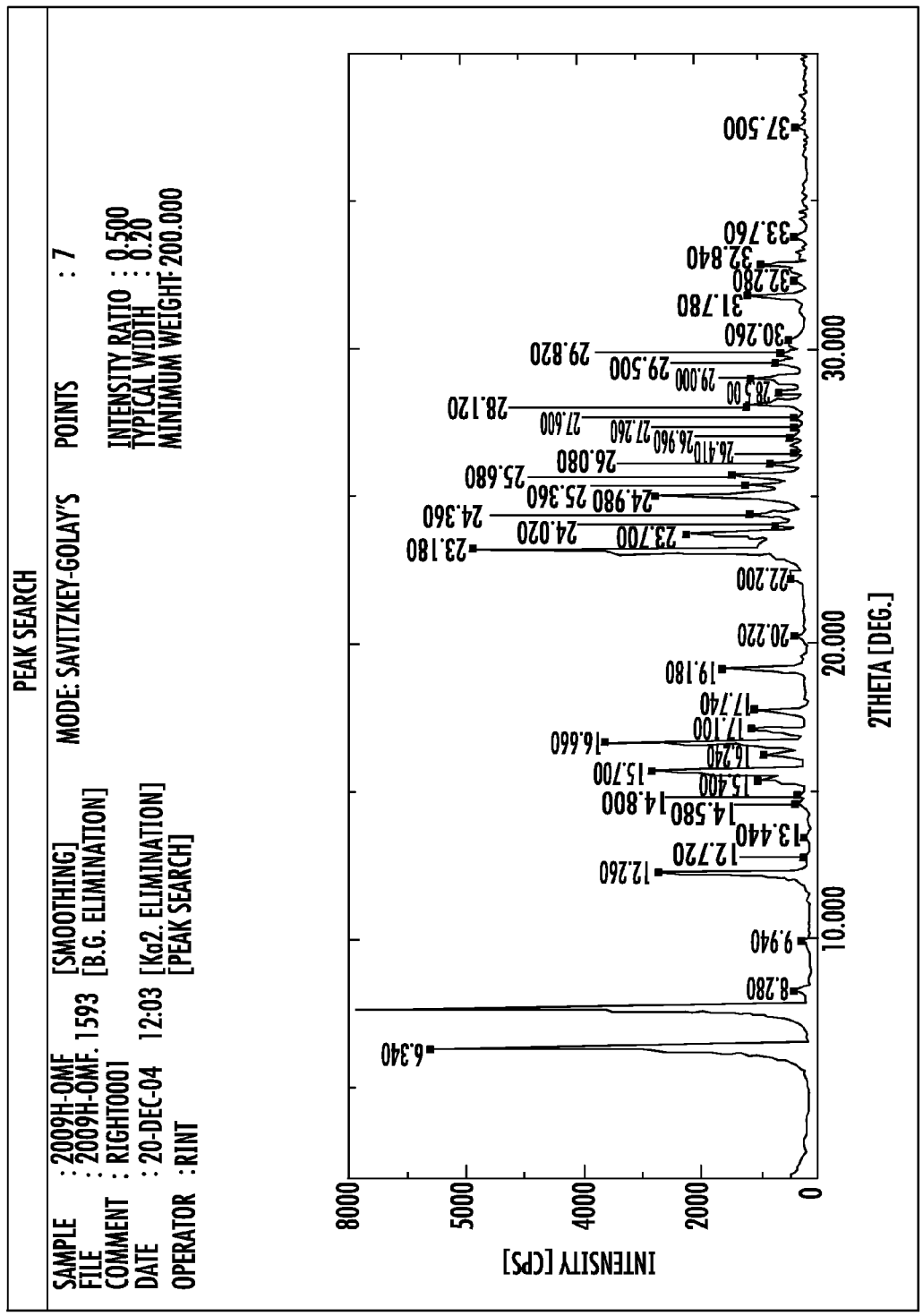
FIG. 4 X-RAY DIFFRACTION PATTERN OF ICOTINIB HYDROCHLORIDE CRYSTALLINE FORM IV (CRYSTALLIZATION FROM N, N-DIMETHYLFORMAMIDE)

PEAK SEARCH

SAMPLE : 2009H-DMF  
DATE : 20-DEC-04 12:03  
FILE OPERATOR :  
: 2009H-OMF.1693  
:RINT  
COMMENT : RIGHT001

| PEAK NO | 2THETA | FWHM | D-VALUE | INTENSITY | I/I0 | PEAK No. | 2THETA | FWHM | D-VALUE | INTENSITY | I/I0 |
|---|---|---|---|---|---|---|---|---|---|---|---|
| 1 | 6.340 | 0.141 | 13.9295 | 5612 | 84 | 31 | 28.120 | 0.188 | 3.1707 | 1152 | 15 |
| 2 | 7.650 | 0.141 | 11.5318 | 7855 | 100 | 32 | 28.500 | 0.141 | 3.1293 | 597 | 8 |
| 3 | 8.280 | 0.212 | 10.6696 | 381 | 5 | 33 | 29.000 | 0.165 | 3.0764 | 1092 | 14 |
| 4 | 9.940 | ***** | 8.8912 | 215 | 3 | 34 | 29.500 | 0.188 | 3.0254 | 656 | 8 |
| 5 | 12.260 | 0.141 | 7.2134 | 2675 | 34 | 35 | 29.820 | 0.235 | 2.9937 | 545 | 7 |
| 6 | 12.720 | ***** | 6.9536 | 224 | 3 | 36 | 30.260 | 0.188 | 2.9512 | 424 | 5 |
| 7 | 13.440 | ***** | 6.5826 | 197 | 3 | 37 | 31.780 | 0.165 | 2.8134 | 1132 | 14 |
| 8 | 14.580 | 0.165 | 6.0704 | 359 | 5 | 38 | 32.280 | 0.188 | 2.7709 | 335 | 4 |
| 9 | 14.880 | 0.188 | 5.9487 | 338 | 4 | 39 | 32.840 | 0.141 | 2.7250 | 896 | 11 |
| 10 | 15.400 | 0.141 | 5.7490 | 1003 | 13 | 40 | 33.750 |  | 2.6528 | 346 | 4 |
| 11 | 15.700 | 0.188 | 5.6398 | 2796 | 36 | 41 | 37.500 | ***** | 2.3963 | 286 | 4 |
| 12 | 16.240 | 0.141 | 5.4534 | 943 | 12 |  |  |  |  |  |  |
| 13 | 16.660 | 0.165 | 5.3169 | 3581 | 46 |  |  |  |  |  |  |
| 14 | 17.100 | 0.155 | 5.1811 | 1135 | 14 |  |  |  |  |  |  |
| 15 | 17.740 | 0.141 | 4.9956 | 1047 | 13 |  |  |  |  |  |  |
| 16 | 19.180 | 0.165 | 4.6236 | 1600 | 20 |  |  |  |  |  |  |
| 17 | 20.220 | 0.141 | 4.3881 | 379 | 5 |  |  |  |  |  |  |
| 18 | 22.200 | 0.118 | 4.0010 | 404 | 5 |  |  |  |  |  |  |
| 19 | 23.180 | 0.165 | 3.8340 | 5797 | 74 |  |  |  |  |  |  |
| 20 | 23.700 | 0.212 | 3.7511 | 2133 | 27 |  |  |  |  |  |  |
| 21 | 24.020 | 0.155 | 3.7018 | 669 | 9 |  |  |  |  |  |  |
| 22 | 24.360 | 0.165 | 3.6509 | 1136 | 14 |  |  |  |  |  |  |
| 23 | 24.980 | 0.165 | 3.5617 | 2710 | 34 |  |  |  |  |  |  |
| 24 | 25.360 | 0.141 | 3.5092 | 1228 | 16 |  |  |  |  |  |  |
| 25 | 25.680 | 0.188 | 3.4562 | 1427 | 18 |  |  |  |  |  |  |
| 26 | 26.080 | 0.188 | 3.4130 | 749 | 10 |  |  |  |  |  |  |
| 27 | 26.440 | 0.141 | 3.3682 | 352 | 4 |  |  |  |  |  |  |
| 28 | 26.960 | 0.212 | 3.3044 | 409 | 5 |  |  |  |  |  |  |
| 29 | 27.260 | 0.141 | 3.2687 | 313 | 4 |  |  |  |  |  |  |
| 30 | 27.600 | 0.118 | 3.2292 | 327 | 4 |  |  |  |  |  |  |

*FIG. 4 CONT.* X-RAY DIFFRACTION PATTERN OF ICOTINIB HYDROCHLORIDE CRYSTALLINE FORM IV (CRYSTALLIZATION FROM N, N-DIMETHYLFORMAMIDE)

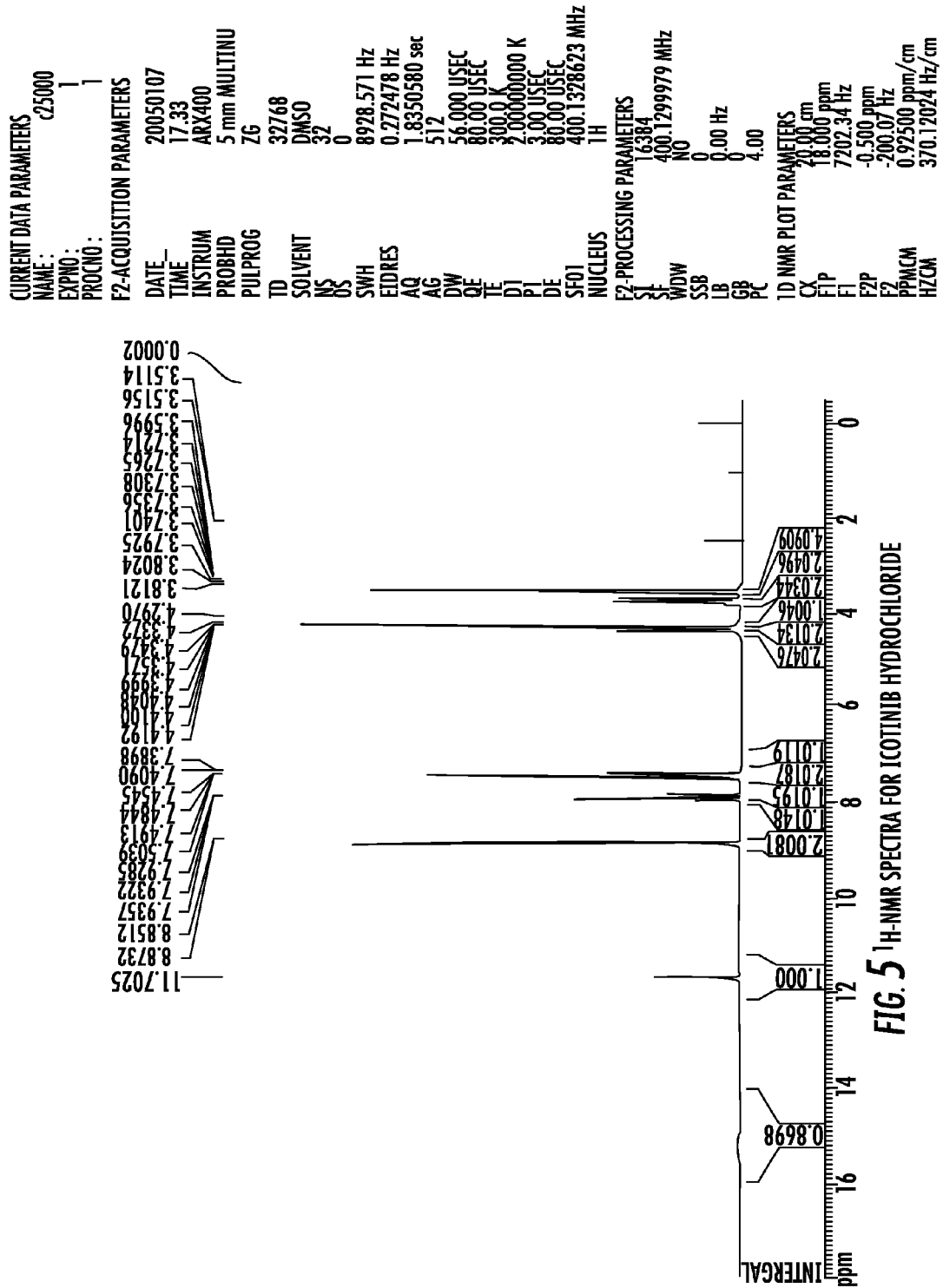
FIG. 5 1H-NMR SPECTRA FOR ICOTINIB HYDROCHLORIDE

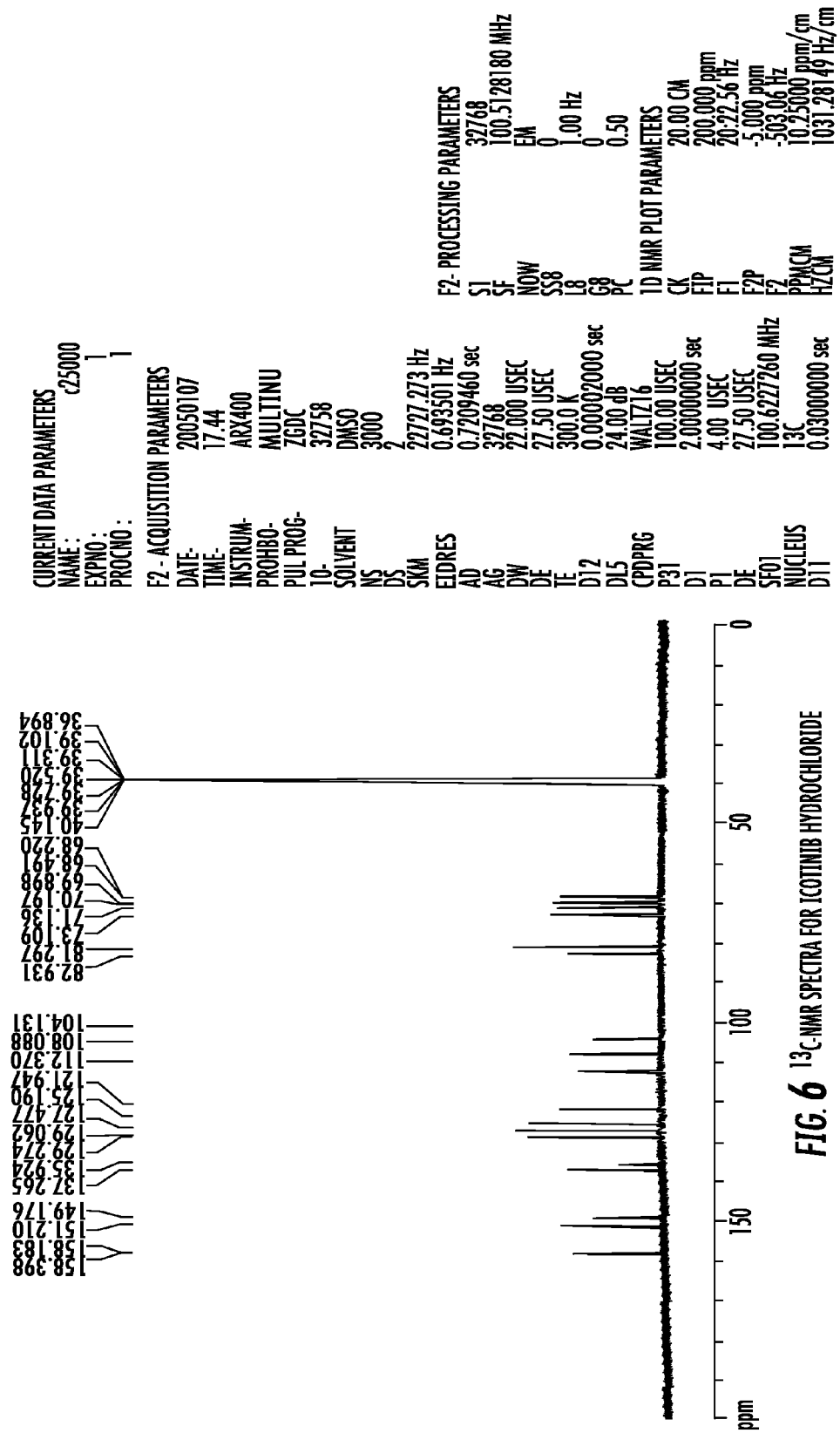

ICOTINIB HYDROCHLORIDE, SYNTHESIS, CRYSTALLINE FORMS, PHARMACEUTICAL COMPOSITIONS, AND USES THEREOF

CROSS REFERENCE TO RELATED APPLICATIONS

This application is a national phase application and claims the benefit, under 35 U.S.C. §371, of PCT/CN2009/000773, filed on Jul. 7, 2009, which in turn claims priority to CN Application No. 200810132631.3, filed on Jul. 8, 2008; CN Application No. 200810131458.7, filed on Jul. 17, 2008; and CN Application No. 200810188272.3, filed on Dec. 23, 2008. All these applications are incorporated herein by reference in their entireties.

FIELD OF THE INVENTION

The present invention relates to 4-[(3-ethynylphenyl)amino]-6,7-benzo-12-crown-quinazoline hydrochloride and new crystalline forms thereof, the present invention also relates to methods for synthesizing this compound, pharmaceutical compositions containing this compound, use of the compound for the treatment of cancer and the relevant intermediates therefor.

BACKGROUND OF THE INVENTION

Tyrosine kinase receptors are trans-membrane proteins that, in response to an extracellular stimulus, propagate a signaling cascade to control cell proliferation, angiogenesis, apoptosis and other important features of cell growth. One class of such receptors, epidermal growth factor receptor (EGFR) tyrosine kinases, are over-expressed in many human cancers, including brain, lung, liver, bladder, breast, head and neck, esophagus, gastrointestinal, breast, ovary, cervix or thyroid cancer.

EGFR is expressed in many types of tumor cells. Binding of cognate ligands (including EGF, TGFα (i.e., Transforming Growth Factor-α) and neuregulins) to the extracellular domain causes homo- or heterodimerization between family members; the juxtaposition of cytoplasmic tyrosine kinase domains results in transphosphorylation of specific tyrosine, serine and threonine residues within each cytoplasmic domain. The formed phosphotyrosines act as docking sites for various adaptor molecules and subsequent activation of signal transduction cascades (Ras/mitogen-activated, PI3K/Akt and Jak/STAT) that trigger proliferative cellular responses.

Various molecular and cellular biology and clinical studies have demonstrated that EGFR tyrosine kinase inhibitors can block cancer cell proliferation, metastasis and other EGFR-related signal transduction responses to achieve clinical anti-tumor therapeutic effects. Two oral EGFR kinase inhibitors with similar chemical structures are Gefitinib (Iressa; Astra-Zeneca), approved by the U.S. FDA for advanced non-small cell lung cancer in 2003 (and later withdrawn), and Erlotinib Hydrochloride (Tarceva; Roche and OSI), approved by the U.S. FDA for advanced non-small cell lung cancer and pancreatic cancer treatment in 2004.

Chinese Patent Publication No. CN1305860C discloses the structure of 4-[(3-ethynyl-phenyl)amino]-6,7-benzo-12-crown-quinoline (free base) on page 29, Example 15, Compound 23.

BRIEF DESCRIPTION OF THE INVENTION

One purpose of the present invention is to provide the hydrochloride salt of 4-[(3-ethynyl-phenyl)amino]-6,7-benzo-12-crown-quinazoline, shown below as Formula I:

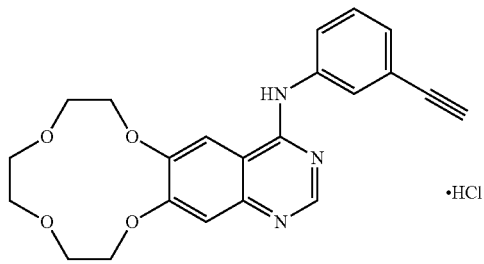 [SMILES: C#Cc1cccc(Nc2ncnc3cc4c(cc23)OCCOCCOCCO4)c1 ; Cl]

Formula I

The inventors unexpectedly discovered that the compound of Formula I above could exist in more than one crystal form. These crystalline forms are referred as Crystalline Forms I, II, III and IV. The compound of Formula I and its Crystalline Forms have better solubility and chemical stability, making them preferable for clinical applications. For the convenience of discussion, the compound of Formula I, "4-[(3-ethynyl-phenyl)amino]-6,7-benzo-12-crown-quinazoline hydrochloride", will hereinafter be referred to as "Icotinib hydrochloride", and its free base, "4-[(3-ethynyl-phenyl)amino]-6,7-benzo-12-crown-quinazoline", will hereinafter be referred to as "Icotinib".

In one aspect, the present invention provides Crystalline Form I of Icotinib hydrochloride. As shown in FIG. 1, Crystalline Form I's X-ray powder diffraction spectra typically have the following peak diffraction angles (where "spacing" is shown as the "d-value" in FIG. 1):

| Peak # | Diffraction angle (2θ°) | Spacing | Relative intensity |
| --- | --- | --- | --- |
| 1 | 5.740 | 15.3841 | 100 |
| 2 | 10.720 | 8.2459 | 13 |
| 3 | 11.500 | 7.6884 | 10 |
| 4 | 21.400 | 4.1487 | 17 |
| 5 | 22.980 | 3.8669 | 12 |

Crystalline Form I of Icotinib hydrochloride is a rather stable crystalline form, consisting of well distributed fine particles with an average particle size ($D_{90}$) of approximately 1-10 μm and can be easily manufactured to the drug product for clinical use.

In another aspect, the present invention is directed to Crystalline Form II of Icotinib hydrochloride. As shown in FIG. 2, Crystalline Form II's X-ray powder diffraction spectra typically have the following peak diffraction angles (where "spacing" is shown as the "d-value" in FIG. 2):

| Peak # | Diffraction angle (2θ°) | Spacing | Relative intensity |
| --- | --- | --- | --- |
| 1 | 7.460 | 11.8405 | 46 |
| 2 | 15.040 | 5.8857 | 30 |
| 3 | 16.240 | 5.4534 | 31 |
| 4 | 22.460 | 3.9553 | 100 |
| 5 | 22.840 | 3.8903 | 47 |

In yet another aspect, the present invention is directed to Crystalline Form III of Icotinib hydrochloride. As shown in FIG. 3, the X-ray powder diffraction spectra of Crystalline Form III typically have the following peak diffraction angles (where "spacing" is shown as the "d-value" in FIG. 3):

| Peak # | Diffraction angle (2θ°) | Spacing | Relative intensity |
| --- | --- | --- | --- |
| 1 | 9.720 | 9.0919 | 100 |
| 2 | 10.400 | 8.4989 | 53 |

In still yet another aspect, the present invention is directed to Crystalline Form IV of Icotinib hydrochloride. As shown in FIG. 4, the X-ray powder diffraction spectra of Crystalline Form IV typically have the following peak diffraction angles (where "spacing" is shown as the "d-value" in FIG. 4):

| Peak # | Diffraction angle (2θ°) | Spacing | Relative intensity |
| --- | --- | --- | --- |
| 1 | 6.340 | 13.9295 | 84 |
| 2 | 7.660 | 11.5318 | 100 |
| 3 | 12.260 | 7.2134 | 34 |
| 4 | 15.700 | 5.6398 | 36 |
| 5 | 16.660 | 5.3169 | 46 |
| 6 | 23.180 | 3.8340 | 74 |
| 7 | 24.980 | 3.5617 | 34 |

For Crystalline Forms I, II, III, and IV described above, only the main peaks (i.e., the most characteristic, significant, unique and/or reproducible peaks) are summarized; additional peaks can be obtained from the diffraction spectra by conventional methods. The main peaks described above can be reproduced within the margin of error (±2 at the last given decimal place, or ±0.2 at the stated value).

Another purpose of the present invention is to provide methods for preparing the compound of Formula I (Icotinib hydrochloride):

Method 1:

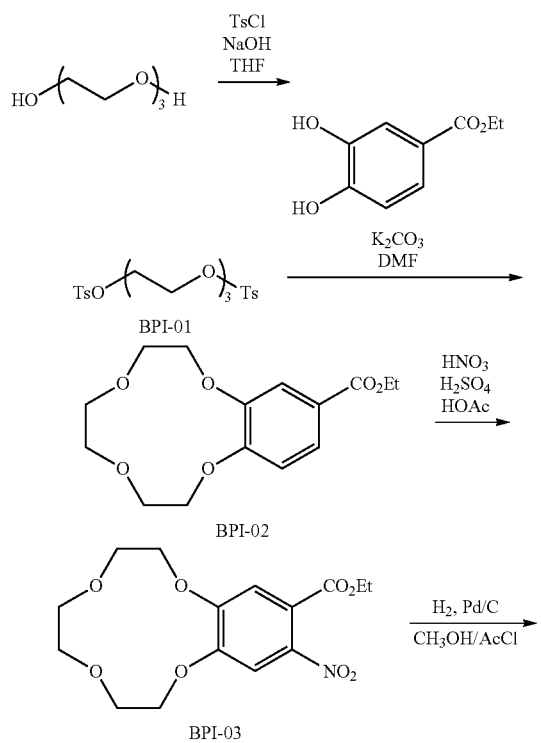

Method 2:

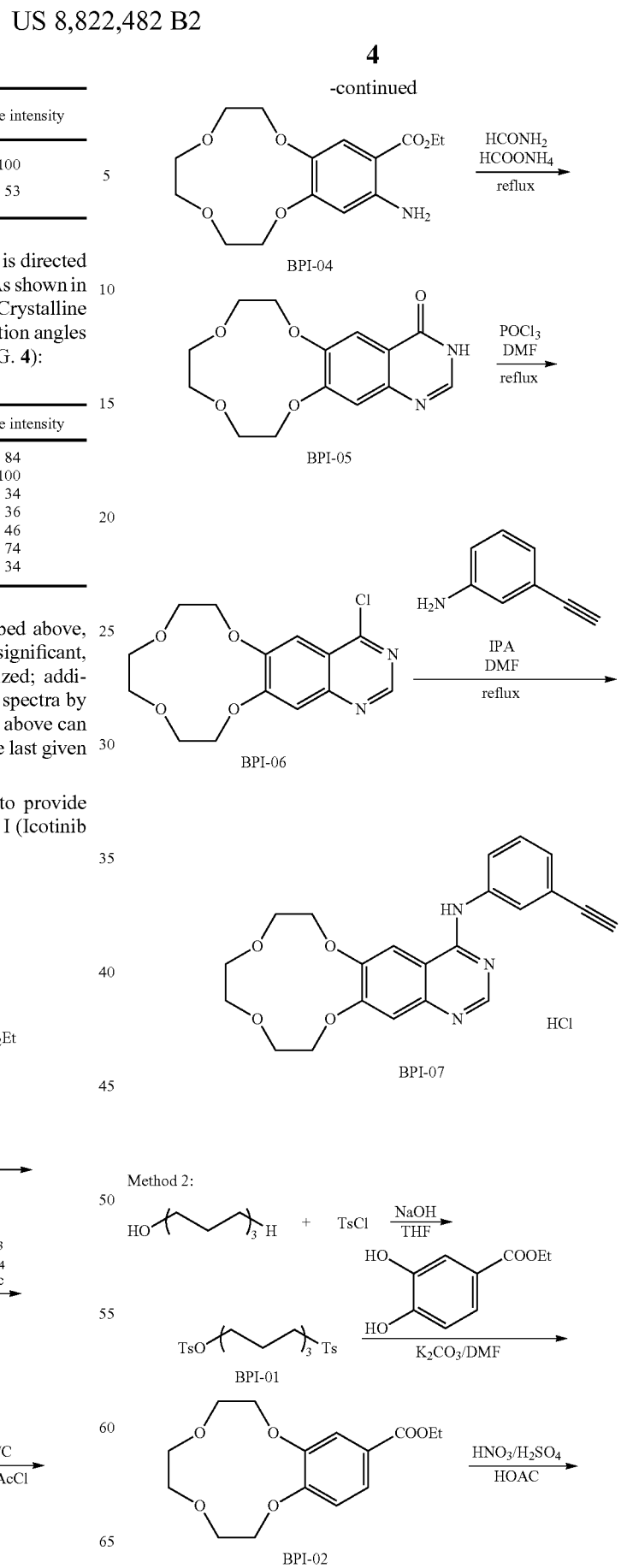

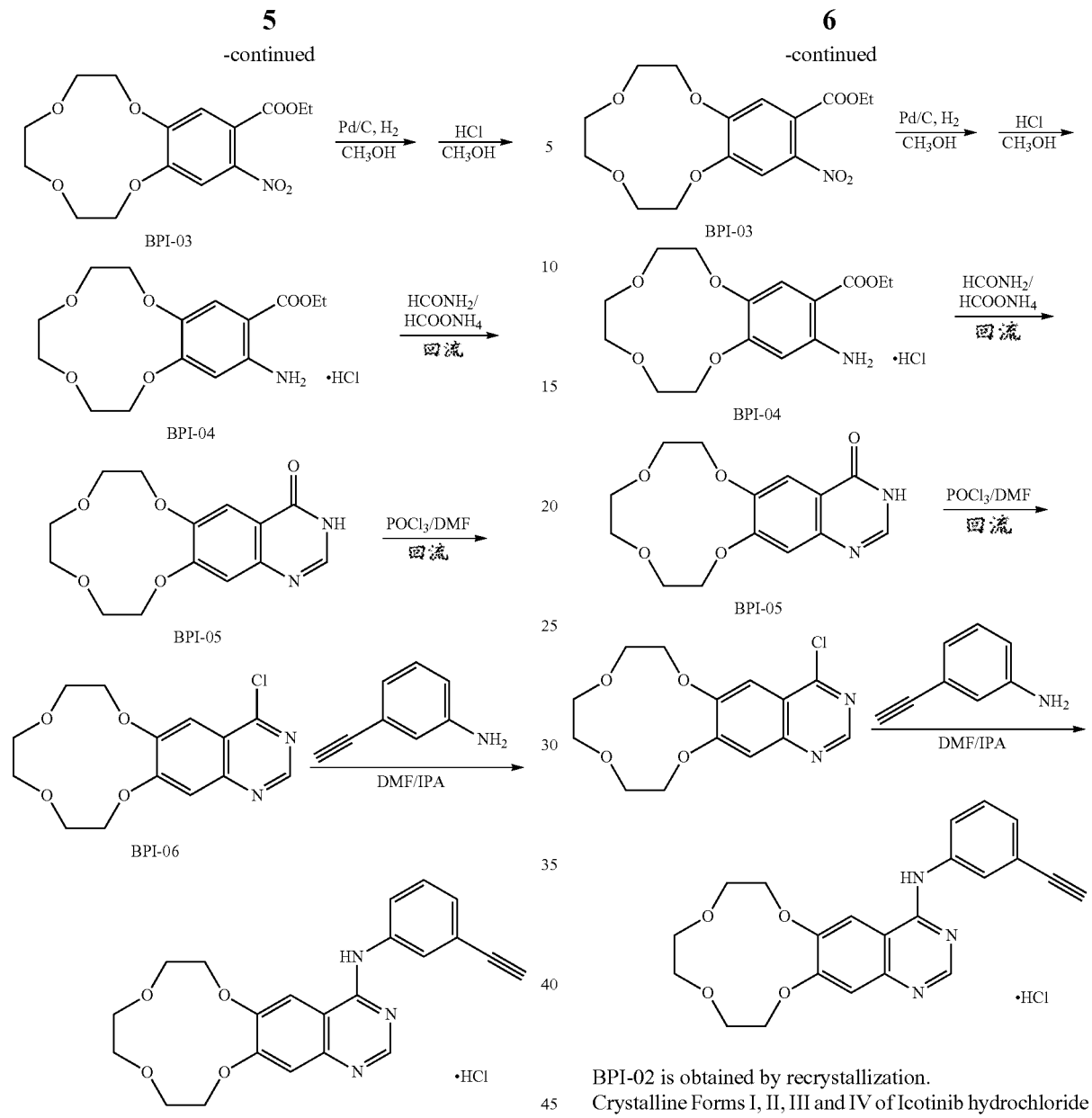

BPI-02 is obtained by recrystallization.

Crystalline Forms I, II, III and IV of Icotinib hydrochloride provided by the present invention can be prepared by the following method: 4-[(3-ethynyl-phenyl)amino]-6,7-benzo-12-crown-quinazoline hydrochloride is refluxed with a polar solvent until completely dissolved. After filtration, cooling, crystallization, filtration and drying, the corresponding different crystalline forms are obtained. Specific crystallization processes are described in the Examples section of the present invention.

The crystallization described above can be carried out in a single solvent, a mixture of solvents or in a mixture of water and organic solvent.

Suitable polar solvents for the crystallization can be selected from, but are not limited to, water, low carbon alcohols, ketones, ethers, esters, halogenated hydrocarbons, alkanes, halogenated benzene, aliphatic nitrile and other aromatic solvents. Preferred solvent can be, e.g., isopropanol, ethyl acetate, 50% ethanol, water, N,N-dimethylformamide, methanol, ethanol, acetone, or propanol.

The term "low carbon alcohols" herein includes straight-chain or branched-chain $C_1$-$C_5$ alcohols, such as straight chain or branched-chain $C_2$-$C_3$ alcohols. Specific examples include methanol, ethanol, isopropanol, and butanol.

Method 3:

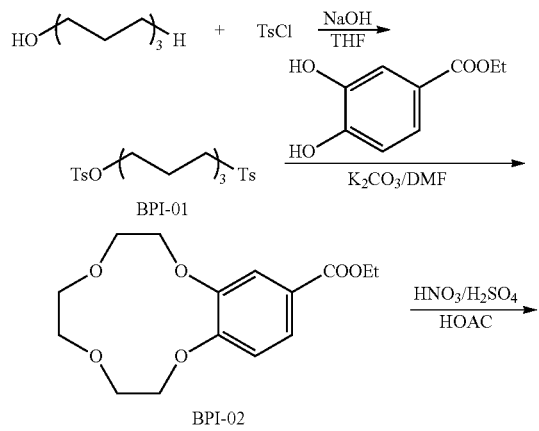

The crystallization of the crystalline forms of the present invention can be conducted in an appropriate solvent system containing at least one solvent by evaporation, cooling and/or by addition of anti-solvents (solvents that are less able to solubilize the Icotinib hydrochloride than those described in the present invention) to achieve super-saturation in the solvent system.

Crystallization may be done with or without seed crystals, which is described in the present invention.

The individual crystalline forms provided by the present invention develop under specific conditions dependent on the particular thermodynamic and equilibrium properties of the crystallization process. Therefore, any technical experts in this area will know that the formed crystals are a consequence of the kinetic and thermodynamic properties of the crystallization process. Under certain conditions (e.g., solvent, temperature, pressure, and concentration of the compound of this invention), a particular crystalline form may be more stable than another crystalline form (or in fact more stable than any other crystalline forms). However, the relatively low thermodynamic stability of particular crystals may have advantageous kinetics. Additional factors other than kinetics, such as time, impurity distribution, stirring, and the presence or absence of seed crystals, etc., may also affect the crystalline form.

In another aspect, the present invention provides pharmaceutical compositions each containing an effective amount of one or more compounds selected from Icotinib hydrochloride and above-described Crystalline Forms I, II, III and IV, as well as a pharmaceutically acceptable carrier. The active compound(s) can be 1-99% (by weight), preferably 1-70% (by weight), or more preferably 10-30% (by weight), of the composition.

The pharmaceutical compositions can be administered orally in forms such as tablets, capsules, pills, powders, sustained release forms, solutions and/or suspensions; by non-intestinal injection in such form as a sterile solution, suspension or emulsion; through a local treatment form such as paste, cream, or ointment; or via a rectal form such as suppositories. The pharmaceutical compositions may be in a unit dosage form that is suitable for precise dosing applications. In addition, the pharmaceutical compositions may include other active ingredients.

Suitable pharmaceutical carriers include water, various organic solvents and various inert diluents or fillers. If necessary, the pharmaceutical compositions may contain various additives, such as spices, adhesives and excipients. For oral administration, tablets can contain various excipients such as citric acid, a variety of disintegrant agents such as starch, alginic acid, and some silicates, and a variety of adhesives such as sucrose, gelatin and Arabic gum. In addition, lubricants including magnesium stearate and talc fillers are commonly used in the production of tablets. The same types of solid components can also be used to formulate soft and hard gelatin capsules. When an aqueous suspension is needed for oral administration, the active compound can be mixed with a variety of sweeteners or flavoring agents, pigments or dye combinations. If necessary, a variety of emulsifiers can be employed or suspensions generated; diluents such as water, ethanol, propylene glycol, glycerin, or their combination can be utilized.

The above-described pharmaceutical compositions are preferably administered orally.

The above-described pharmaceutical compositions are preferably in the tablet or capsule form.

In another aspect, the present invention provides use of the compounds of this invention (i.e., Icotinib hydrochloride and its above-described Crystalline Forms I, II, III and IV) in the manufacturing of medicaments that are useful for the treatment or prevention of non-malignant over-hyperplasia diseases in mammals. The non-malignant over-hyperplasia diseases can be a benign skin hyperplasia or a benign prostatic hyperplasia.

In yet one aspect, the present invention provides use of the compounds of this invention (i.e., Icotinib hydrochloride and its above-described Crystalline Forms I, II, III and IV) in the manufacturing of medicaments that are useful for the treatment or prevention of mammalian pancreatitis, kidney disease, cancer, angiogenesis or angiogenesis-related diseases.

In yet another further aspect, the present invention provides use of the compounds of this invention (i.e., Icotinib hydrochloride and its above-described Crystalline Forms I, II, III and IV) in the manufacturing of medicaments that are useful for mammalian embryo cell transplantation.

Icotinib hydrochloride and its Crystalline Forms I, II, III and IV of this invention can be used to treat or prevent diseases selected from, but not limited to, tumor angiogenesis, chronic inflammatory diseases such as rheumatoid arthritis, atherosclerosis, skin diseases such as psoriasis and scleroderma, diabetes-induced skin diseases, diabetic retinopathy, premature retinopathy, age-related degeneration stains, hemangioma, glioma, Kaposi internal tumor, ovarian cancer, breast cancer, lung cancer, pancreatic cancer, lymphoma, prostate, colon and skin tumors and their complications.

Among the mammals mentioned herein, human beings are preferred.

Another purpose of this invention is to provide a method for treating malignant tissue hyperplasia in mammals. This treatment method includes application of an effective amount of Icotinib hydrochloride and/or its Crystalline Forms and/or the pharmaceutical compositions described above to mammalian patients with hyperplasia disease. In some embodiments, the treatment method also includes use of MMP (matrix metalloproteinase) inhibitor, VEGFR (vascular endothelial growth factor receptor) kinase inhibitors, HER2 inhibitor, VEGFR antibody drugs, and/or endostatin drugs. In some other embodiments, the treatment method also includes using one or more anti-tumor agents such as mitotic inhibitors, alkylating agents, anti-metabolites, tumor antibiotics, growth factor inhibitors, cell cycle inhibitors, enzymes, enzyme inhibitors, biological response modifiers, anti-hormone drugs and so on. The anti-tumor agents can be selected from carboplatin, paclitaxel, gemcitabine, methotrexate, 5-FU, camptothecin, cyclophosphamide, BCNU and other medications.

Another aspect of this invention is to provide a method for the treatment of diseases caused by tyrosine kinase dysfunction. This treatment method includes administering to an patient with the disease caused by tyrosine kinase dysfunction an effective amount of Icotinib hydrochloride and/or one or more of its Crystalline Forms and/or the pharmaceutical compositions of this invention. The tyrosine kinase dysfunction-related diseases include, but are not limited to disease of brain, lung, liver, bladder, breast, head and neck, esophagus, gastrointestinal tract, breast, ovary, cervix or thyroid tumors and their complications.

Target diseases for the just described treatment method are preferably selected from brain cancer, lung cancer (such as non-small cell lung cancer (NSCLC)), kidney cancer, bone cancer, liver cancer, bladder cancer, chest cancer, neck cancer, esophageal cancer, gastric cancer, colon cancer, rectal cancer, breast cancer, ovarian cancer, melanoma, skin cancer, adrenal cancer, cervical cancer, lymphoma, or thyroid tumors and their complications.

The above-described methods can be applied in combination with any chemical therapy, biological therapy, or radiation therapy.

The above-described treatment method can further include application of anti-EGFR antibodies, anti-EGF antibodies, or both, in the same treatment.

The dosage of the active ingredient or compound when administered will be determined by the individual needs of the patient to be treated, administration route, severity of disease or illness, dosing schedule, as well as evaluation and judgment of the designated doctor. However, based on the active compound, the preferred range of the effective dosage can be approximately 0.01-120 mg daily per kilogram of body weight; or more preferably 1-50 mg per day per kilogram of body weight in single or separate doses. In some cases, it is more suitable to apply the lower end of the above-described dosage range, while in other cases the higher dosages may be used without causing harmful side effects.

Another aspect of the present invention is to provide 4-[(3-ethynyl-phenyl)amino]-6,7-benzo-12-crown-quinazoline hydrochloride for clinical applications. In particular, the present invention relates to clinical treatment with Icotinib hydrochloride with the following treatment options for cancer patients: the dosage of Icotinib hydrochloride and/or Crystalline Form I, II, III or IV can be 25-2100 mg/day with the administration frequency being 1-3 times a day; a preferred dosage is 75-1200 mg/day with the administration frequency being 1-3 times a day; a more preferred dosage is 75-1200 mg/day with the administration frequency being 2-3 times/day; an even more preferred dosage is 100-1200 mg/day with the administration frequency being 2-3 times a day.

BRIEF DESCRIPTIONS OF THE DRAWINGS

FIG. 1 shows the X-ray diffraction pattern of Icotinib hydrochloride Crystalline Form I (crystallization from isopropanol).

FIG. 2 shows the X-ray diffraction pattern of Icotinib hydrochloride Crystalline Form II (crystallization from 50% ethanol).

FIG. 3 shows the X-ray diffraction pattern of Icotinib hydrochloride Crystalline Form III (crystallization from an aqueous solvent).

FIG. 4 shows the X-ray diffraction pattern of Icotinib hydrochloride Crystalline Form IV (crystallization from N,N-dimethylformamide).

FIG. 5 is a $^1$H-NMR spectra for Icotinib hydrochloride.

FIG. 6 is a $^{13}$C-NMR spectra for Icotinib hydrochloride.

EXAMPLES

The following specific examples and the efficacy tests further describe the present invention. They shall not limit or restrict the scope of the present invention in any way.

Example 1

Step 1

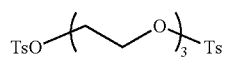

BPI-01

Preparation: 16 kg (400 mol) of sodium hydroxide was dissolved in 80 L of water in a 400 L reactor, and then 18.8 L (140 mol) of triethylene glycol, 32 L of THF were added into the reactor. After cooling below 5° C., a solution of 47.84 kg (260 mol) of tosyl chloride and 50 L of THF was added dropwise. Following the addition, the reaction mixture was kept at this temperature for 2 hours, and it was then poured into 240 L of ice water. The precipitate was formed and filtered, washed with a small amount of water, and dried. 58.64 kg of BPI-01 as a white crystalline powder was yielded at 91.4%. mp: 77-80° C., HPLC: 97%. TLC (petroleum ether:ethyl acetate=1:1) Rf=0.87.

NMR data: $^1$H-NMR (CDCl$_3$): δ ppm: 7.78 (d, 4H, J=10.4 Hz, benzene protons by sulfonyl group); 7.34 (d, 4H, J=11.6 Hz, benzene protons by methyl group); 4.129 (dd, 4H, J=5.6 Hz, ethylene protons by the sulfonyl group); 3.64 (dd, 4H, J=5.6 Hz, ethylene protons away from the sulfonyl group); 3.517 (s, 4H, ethylene protons in the middle); 2.438 (s, 6H, methyl protons on the benzene).

Step 2

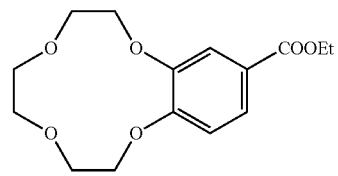

BPI-02

Preparation: A solution containing 3.64 kg (20 mol) of ethyl 3,4-dihydroxybenzoate and 12.4 kg (89.6 mol) of potassium carbonate in 300 L of N,N-dimethylformamide was stirred and heated to 85-90° C. for about 30 minutes. A solution of 917 kg (20 mol) of BPI-01 in 40 L of N,N-dimethylformamide was added dropwise over 1.5-2 hours. After the addition, the reaction was kept for 30 minutes; the reaction completion was confirmed by TLC (developing solvent:petroleum ether:ethyl acetate=1:1, Rf=0.58). The reaction mixture was removed from the reactor and filtered. Then, the filtrate was evaporated to remove N,N-dimethylformamide; 240 L of ethyl acetate was added to dissolve the residue. After filtration and vacuum evaporation, the residual solution was extracted with 300 L of petroleum ether. After evaporation of the petroleum ether, the residual solids were re-crystallized with isopropanol in a ratio of 1:2.5 (W/V); 1.68 kg of BPI-02 as a white powder was obtained in a yield of 28%. mp: 73-76° C., HPLC: 96.4%.

NMR data: $^1$H-NMR (CDCl$_3$): δ ppm: 7.701 (d, 1H, J=2.4 Hz, benzene proton at position 6); 7.68 (s, 1H, benzene proton at position 2); 6.966 (d, 1H, J=10.8 Hz, benzene proton at position 5); 4.374-3.81 (q, 2H, J=9.6 Hz, methylene protons of the ethyl); 3.78-4.23 (dd, 12H, J=4.8 Hz, crown ether protons); 1.394 (t, 3H, J=9.6 Hz, methyl protons of the ethyl).

MS: m/z 296.

Step 3

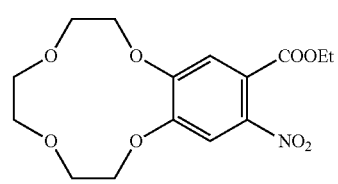

BPI-03

Preparation: A solution of 592 g (2 mol) of BPI-02 and 600 mL of acetic acid in a 5 L reaction flask was cooled to 0° C.; 1640 mL (25.4 mol) of concentrated nitric acid was slowly added. The internal temperature should not exceed 10° C. While cooled below 0° C., 1 L of concentrated sulfuric acid was added dropwise. The internal temperature should not be higher than 5° C. After the addition, the reaction was kept at 0-5° C. for 1-2 hours. After completion of the reaction, the reaction solution was poured into 15 L of ice water in a plastic bucket. After mixing, filtration, and re-crystallization in ethanol, 449 g of BPI-03 as a light yellow to yellow crystalline powder was obtained in 65.7% yield. mp: 92-95° C., HPLC: 98.2%. TLC (petroleum ether:ethyl acetate=1:1) Rf=0.52.

NMR data: $^1$H-NMR (CDCl$_3$): δ ppm: 7.56 (s, 1H, benzene proton at position 5); 7.20 (s, 1H, benzene proton at position 2); 4.402 (q, 2H, J=9.2 Hz, methylene protons of the ethyl); 4.294 (dd, 12H, J=4.8 Hz, crown ether protons); 1.368 (t, 3H, J=92 Hz, methyl protons of the ethyl).

Step 4

BPI-04

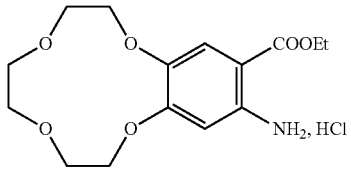

Preparation: In a 3 L hydrogenation reactor, 2 L of methanol and 195 g (0.57 mol) of BPI-03 were added, and then 63 mL of acetyl chloride was slowly added. After a short stir, 33 g of Pd/C containing 40% water was added. The reaction was conducted under 4 ATM hydrogen until hydrogen absorption stopped, and then the reaction was kept for 1-2 hours. After completion of the reaction, the reaction mixture was transferred into a 5 L reactor. After filtration, crystallization, and filtration, the product was obtained. The mother liquor was concentrated under vacuum, and more product was obtained. The combined crops were 168 g of BPI-04 as a white to pink crystalline powder in a yield of 85%. mp: 198-201° C., HPLC: 99.1%. TLC (petroleum ether:ethyl acetate=1:1) Rf=0.33.

NMR data: $^1$H-NMR (DMSO-d$_6$): δ ppm: 8-9 (br., 3H, 2 protons of the amino group and a proton of the hydrochloric acid); 7.37 (s, 1H, benzene proton at position 5); 6.55 (s, 1H, benzene proton at position 2); 4.25 (q, 2H, J=7.06 Hz, methylene protons of the ethyl); 4.05 (dd, 12H, J=4.04 Hz, crown ether protons); 1.31 (t, 3H, J=7.06 Hz, methyl protons of the ethyl).

Step 5

BPI-05

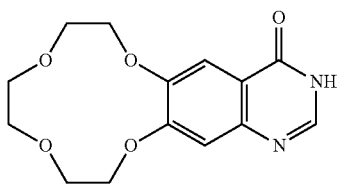

Preparation: 1105 g (3.175 mol) of BPI-04, 4810 g (106.9 mol) of formamide, and 540 g (8.55 mol) of ammonium formate were added to a 10 L 3-neck bottle. The reaction mixture was heated to 165° C. under reflux for 4 hours. After cooling to room temperature, 3 L of water was added, and then the mixture was stirred for 10 minutes. After filtration, washing, and drying, 742 g of BPI-05 as a white crystalline powder was obtained in a yield of 80%. mp: 248-251° C., HPLC: 99.78%. TLC (chloroform:methanol=8:1) Rf=0.55.

NMR data: 1H-NMR (DMSO-d$_5$): δ ppm: 12.06 (s, 1H, NH of the quinazoline); 8.0 (d, 1H, J=3.28 Hz, proton of the quinazoline position 3); 7.62 (s, 1H, proton of the quinazoline position 6); 7.22 (s, 1H, proton of the quinazoline position 9); 4.25 (dd, 12H, J=4.08 Hz, crown ether protons).

Step 6

BPI-06

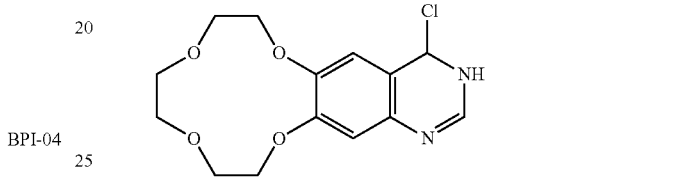

Preparation: 337 g (1.13 mol) of BPI-05, 7.1 L of chloroform, 1.83 L (19.58 mol) of POCl$_3$ and 132 ml of N,N-dimethylformamide were added to a 10 L 3-neck bottle. The reaction mixture was stirred at reflux temperature. After dissolution, reaction completion was checked by TLC (developing solvent:chloroform:methanol=15:1, Rf=0.56); the reaction took approximately 8 hours to complete. Then, the reaction solution was cooled and evaporated under vacuum to dryness. The residue was dissolved in 4 L of chloroform; 4 kg of crushed ice was poured into the solution and the mixture was stirred for 0.5 hours. After separation, the aqueous phase was extracted twice with 2 L of chloroform. The organic phases were combined, 4 L of ice water was added and the pH was adjusted with 6 N NaOH to pH 8-9 while the temperature was maintained below 30° C. After separation, the organic phase was washed with saturated NaCl, dried over anhydrous sodium sulfate and the solvents removed by vacuum evaporation. The residual solids were washed with acetone and filtered; 268 g of BPI-06 as a white crystalline powder was obtained in a yield of 77% with mp: 164-167° C. and HPLC purity of 99%.

NMR data: $^1$H-NMR (CDCl$_3$): δ ppm: 8.89 (s, 1H, proton of the quinazoline position 2); 7.68 (s, 1H, proton of the quinazoline position 9); 7.42 (s, 1H, proton of the quinazoline position 6); 4.38-3.81 (dd, 12H, J=3.88 Hz, crown ether protons).

Step 7

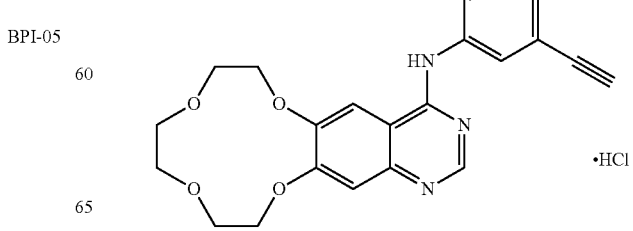

Preparation of the compound of the present invention: To a suspension of 20.8 g of BPI-06 in 500 mL of ethanol was added 25 mL of N,N-dimethylformamide and a solution of 8.98 g m-acetylene aniline in 200 mL of isopropanol. The reaction mixture was stirred at room temperature for 5 minutes until dissolved completely, and then the reaction solution was heated at reflux for 3 hours. After concentration and drying, the residual solids were dissolved in ethyl acetate, washed with water, and dried over anhydrous sodium sulfate. Thus, 27.1 g of the compound of Formula I was obtained as a white crystalline powder.

NMR data: $^1$H-NMR (Bruker APX-400, solvent: DMSO-$d_5$, TMS as internal standard): δ ppm: 3.58 (dd, 2H, two protons of the crown position 12); 3.60 (dd, 2H, two protons of the crown position 13); 3.73 (dd, 2H, two protons of the crown position 10); 3.80 (dd, 2H, two protons of the crown position 15); 4.30 (s, 1H, proton of the alkynyl); 4.34 (dd, 2H, two protons of the crown position 16); 4.40 (dd, 2H, two protons of the crown position 9); 7.39 (d, 1H, benzene proton at position 25); 7.46 (dd, 1H, benzene proton at position 26); 7.49 (s, 1H, proton of the quinazoline position 6); 7.82 (d, 1H, benzene proton at position 27); 7.94 (t due dd, 1H, proton of the quinazoline position 19); 8.85 (s, 1H, benzene proton at the position 23); 8.87 (s, 1H, proton of the quinazoline position 2); 11.70 (s, 1H, proton of the aromatic amine as salt); 14-16 (bs, 1H, hydrochloride), see FIG. 5.

NMR data: $^{13}$C-NMR (DMSO-$d_6$), see FIG. 6.

Mass spectrometry (MS): Instrument: ZAB-HS, testing conditions: EI, 200° C., 700 ev, MS measured molecular weight: m/z 427.

Elemental Analysis of the Final Product:
(1). C, H, N Determination
Instruments: Elementar-Vario EL.

TABLE 1

Results of elemental analysis, compared with the calculated values (%)

|  | Element | | |
| --- | --- | --- | --- |
|  | C | H | N |
| Calculated | 61.70 | 5.15 | 9.81 |
| Detected (1) | 61.75 | 5.25 | 9.79 |
| Detected (2) | 61.71 | 5.25 | 9.77 |
| Average | 61.73 | 5.25 | 9.78 |
| Error | 0.03 | 0.10 | 0.03 |

The errors of C, H, N measured results and calculated values were less than 0.3% and meet the specifications of the final product.

(2). Cl Determination
Instrument: Carlo-Erba1112 elemental analyzer, Chlorine determination: oxygen flask method, standard solution of mercury nitrate: 0.01079 mol/L.

TABLE 2

Results of chlorine test, compared with the calculated values (%)

| Element | Calculated | Detected (1) | Detected (2) | Average | Error |
| --- | --- | --- | --- | --- | --- |
| Cl | 8.30 | 8.53 | 8.43 | 8.48 | 0.18 |

Example 2

Preparation of Icotinib Hydrochloride Crystalline Form I

In a 250 mL round bottom flask, 0.1 g of Icotinib hydrochloride was dissolved in 200 mL of isopropanol, with heating. After filtration, the filtrate was allowed to cool for crystallization. The crystals were filtered, washed with a small amount of acetone and dried under vacuum below 60° C. A white crystalline powder was obtained with mp of 225-228° C.

A powder X-ray diffraction pattern method was used to characterize the structure of Crystalline Form I; see FIG. 1 (TGA Instrument: DSC204 (NETZSCH company)). The TGA result indicated that Icotinib hydrochloride Crystalline Form I had no crystal solvent.

Example 3

Preparation of Icotinib Hydrochloride Crystalline Form II

In a 25 mL of round bottom flask, 0.5 grams of Icotinib hydrochloride was dissolved in 15 mL of 50% ethanol with heating. After filtration, the filtrate was allowed to cool for crystallization. The solids were filtered, washed with 5 mL of acetone and dried under vacuum below 60° C. A white crystalline powder was obtained with mp of 224-227° C.

A powder X-ray diffraction pattern method was used to characterize the structure of Crystalline Form II; see FIG. 2 (TGA Instrument: DSC204 (NETZSCH company)). The TGA result indicated that each molecule of Icotinib hydrochloride Crystalline Form II contained 2.11 molecules of crystal water.

Example 4

Preparation of Icotinib Hydrochloride Crystalline Form III

In a 25 mL round bottom flask, 0.5 g of Icotinib hydrochloric acid was dissolved in 15 mL of water with heating. After filtration, the filtrate was allowed to cool for crystallization. The solids were filtered, washed with 5 mL of acetone and dried under vacuum below 60° C. A white crystalline powder was obtained with mp of 224-227° C.

A powder X-ray diffraction pattern method was used to characterize the structure of Crystalline Form III; see FIG. 3 (TGA Instrument: DSC204 (NETZSCH company)). The TGA result indicated that each molecule of Icotinib hydrochloride Crystalline Form III contained 1.90 molecules of crystal water.

Example 5

Preparation of Icotinib Hydrochloride Crystalline Form IV

In a 25 mL round bottom flask, 0.5 g of Icotinib hydrochloride was dissolved in 10 mL of N,N-dimethylformamide with heating. After filtration, the filtrate was allowed to cool for crystallization. The solids were filtered, washed with 5 mL of acetone, and dried under vacuum below 60° C. A light yellow crystalline powder was obtained with mp of 223-226° C.

A powder X-ray diffraction pattern method was used to characterize the structure of Crystalline Form IV; see FIG. 4 (TGA Instrument: DSC204 (NETZSCH company)). The TGA result indicated that each molecule of Icotinib hydrochloride Crystalline Form IV contained 0.158 molecules of crystalline N,N-dimethylformamide.

Efficacy Tests

Test 1: Inhibition and Selectivity of the EGFR Tyrosine Kinase by Icotinib Hydrochloride Crystalline Form I by Polyacrylamide Gel Electrophoresis Method: This method is based on the ability of protein kinases to catalyze substrate phosphorylation; radioisotope $^{32}$P-labeled ATP ($^{32}$P-γ-ATP) is utilized in the reaction system to radioactively tag the protein substrate with $^{32}$P. After separation and isolation of the protein substrate by polyacrylamide gel electrophoresis, the intensity of the radioactive $^{32}$P-labeled protein substrate is recorded.

The EGFR tyrosine kinase (2.4 μg/μl, 14.5 units/μg, Sigma) and Crk (EGFR substrate, 32 ng/μl) were mixed in 25 μl of kinase reaction buffer. The kinase reaction buffer included 1 μM of non-isotope labeled-ATP. The above-mentioned mixture contained different concentrations of Icotinib hydrochloride Crystalline Form I (0, 0.5, 2.5, 12.5, and 62.5 nM). The mixture was incubated on ice for 10 min, and 1 μCi of $^{32}$P-γ-ATP was then added. After incubation at 30° C. for 20 min, SDS (sodium dodecyl sulfate) sample buffer was added, and the mixture was boiled in a 100° C. water bath for 4 min. The samples were separated by 10% SDS-PAGE. After vacuum drying of the polyacrylamide gel, the intensity of radioactively labeled proteins were measured and recorded using a Phosphorimager (Molecular Dynamics Inc.). The signal was quantitatively analyzed utilizing ImageQuant software. The degree of Crk substrate phosphorylation was used to estimate the activity of the kinase.

Inhibition (%)=(1−kinase activity of the test group/ kinase activity of control group)×100%

Results:

(1) Icotinib hydrochloride Crystalline Form I inhibited EGFR tyrosine kinase activity in a dose-response dependent relationship. When the concentration of Icotinib hydrochloride Crystalline Form I was 0.5, 2.5, 12.5 and 62.5 nM, the inhibition rates of EGFR kinase activity were 20.5, 36.6, 63 and 87.6%, respectively. From the dose-response curve, the $IC_{50}$ of Icotinib hydrochloride Crystalline Form I to inhibit EGFR kinase activity (the concentration of the inhibitor when 50% of the activity was inhibited) was 5 nM, similar to the products marketed abroad.

(2) In order to study the selectivity of Icotinib hydrochloride Crystalline Form I for EGFR kinase inhibition, the ability of Icotinib hydrochloride Crystalline Form I to inhibit EGFR and Arg (abl-related gene) tyrosine kinase activities and Crk substrate phosphorylation was compared in parallel using the same methodology. The concentration of 62.5 nM of Icotinib hydrochloride Crystalline Form I did not inhibit the Arg kinase but did inhibit the EGFR kinase by 97% demonstrating the selectivity of the Icotinib hydrochloride Crystalline Form I for the EGFR kinase.

The results described above show that Icotinib hydrochloride Crystalline Form I is a sensitive and selective EGFR kinase inhibitor.

Test 2: Inhibition of EGFR-Mediated Protein Phosphorylation by Icotinib Hydrochloride Crystalline Form I at the Cellular Level Methods: The experiment utilized a high EGFR-expressing cell line, A431 (human epidermoid carcinoma). A431 cells in logarithmic growth phase were seeded into 12-well cell culture plates ($5 \times 10^5$ cells/well); the cells were grown in DMEM cell culture medium (Gibco Company) containing 10% fetal calf serum (FCS) at 37° C. in 5% $CO_2$ for 18 hours. The cells were washed twice with PBS buffer, and DMEM without FCS was then added. After incubating for 18 hours, Icotinib hydrochloride Crystalline Form I in dimethyl sulfoxide (DMSO) was added to individual wells at final concentrations of 0, 10, 50, 250 or 1000 nM. After incubating at 37° C. for 2.5 hours, 100 ng/ml of EGF was added to stimulate the cells for 5 minutes. Cells were then extracted in the presence 1 mM vanadate (inhibits dephosphorylation) to collect total cellular proteins, and proteins were resolved by 10% SDS-PAGE and transferred to nitrocellulose. Following detection of phosphorylated proteins with anti-phosphotyrosine antibodies (PY99 and 4G10, Upstate Biotech) and visualization with a horseradish peroxidase-labeled second antibody (Transduction Laboratories, Inc.) and ECL chemiluminescence (Amersham Corp.), bands were quantified by densitometry. Membranes were then stripped and incubated with anti-EGFR antibodies to compare amounts of EGFR in cells exposed to different concentrations of Icotinib hydrochloride Crystalline Form I as an internal control.

Inhibition (%)=(1−kinase activity of the test group/ kinase activity of control group)×100%

Results: In A431 cells, Icotinib hydrochloride Crystalline Form I inhibited EGF-induced, EGFR tyrosine kinase-mediated intracellular protein tyrosine phosphorylation by 5.4, 52.9, 61.9 and 63.7% at concentrations 10, 50, 250 and 1000 nM, respectively. The median effective concentration ($EC_{50}$) was approximately 50 nM. The results also demonstrated that EGFR expression was not significantly different between cells exposed to different concentration of Icotinib hydrochloride Crystalline Form I, suggesting that the drug did not alter EGFR expression but it only inhibited EGFR kinase activity.

Test 3: Growth Inhibition In Vitro of Human Tumor Cell Lines by Icotinib Hydrochloride Crystalline Form I Tumor cell lines: A431 human epidermoid carcinoma, A549 human non-small cell lung cancer, BEL-7402 human hepatoma, BGC-823 human gastric adenocarcinoma, HCT8 human colon cancer, H460 human lung adenocarcinoma, KB human epidermoid carcinoma.

Method: Cells (~$2 \times 10^3$) were seeded in 96-well plates in 200 μL of RPMI1640 cell culture medium supplemented with 10% FBS. After 24 hours at 37° C. and 5% $CO_2$, the medium was replaced in quintuplicate wells with medium containing Icotinib hydrochloride Crystalline Form I dissolved in DMSO and then serial diluted, yielding final Icotinib concentrations of 0.05-300 μM. DMSO concentrations were less than 0.1% at the highest drug concentrations. Cells were incubated in medium alone with 0.1% DMSO as a negative control. Following a 96 hr incubation, the MTT [3-(4,5-dimethylthiazol-2-yl)-2,5-diphenyltetrazolium] colorimetric assay was performed using a microplate reader (reference wavelength 450 nm, detection wavelength 570 nm). The logarithm of drug concentration on the inhibition rate was linear, and the half inhibitory concentration of the drug ($IC_{50}$) was obtained.

Result: As shown in Table 3, in vitro growth inhibition by Icotinib hydrochloride Crystalline Form I on human tumor cells, including high EGFR-expressing A431 cells, was dose-dependent. The A431 cell line was extremely sensitive, with an $IC_{50}$ of 1 μmol/L, followed by the gastric cancer cell line BGC823, human non-small cell lung cancer cell line A549 and human lung adenocarcinoma cell line H460 with $IC_{50}$'s of 4, 12 and 16 μmol/L, respectively. Icotinib hydrochloride Crystalline Form I had low activity against HCT8, BEL-7402, and KB tumor cells.

TABLE 3

Tumor cell growth inhibition of Icotinib hydrochloride Crystalline Form I

| Cell lines | IC$_{50}$ (μmol/L) |
|---|---|
| A431/human epidermoid carcinoma | 1 |
| BGC-823/human gastric cancer cells | 4.06 |
| A549/human non-small cell lung cancer cells | 12.16 |
| H460/human lung adenocarcinoma cells | 16.08 |
| HCT8/human colon cancer cells | >200 |
| KB/human epidermoid carcinoma cells | 40.71 |
| BEL-7402/human hepatoma cells | >200 |

Test 4: Tumor Inhibition by Icotinib Hydrochloride Crystalline Form I on Human a Tumor Xenograft in Nude Mice This was a preliminary study to compare Icotinib hydrochloride Crystalline Form I with erlotinib hydrochloride on inhibition of human A431 (human epidermoid carcinoma cell line) xenograft tumor.

Methods: The high EGFR-expressing human A431 (human epidermoid carcinoma cell line) cell line was selected for the xenograft study.

Tumor transplantation method: A431 human epidermoid cancer cells were inoculated subcutaneously in the right armpit of BALB/C nude mice to generate tumor nodules. These nodules were harvested, cut into 6 mm$^3$ blocks for routine inoculation and implanted into each mouse for the study. When tumors reached approximately 20 mm$^3$ in size (6-7 days), the animals were randomly divided into 4 groups of 6-9 animals/each group and body weights were recorded. The groups consisted of a control group (no drug treatment), an erlotinib hydrochloride treatment group (200 mg/kg) and high and low dose Icotinib hydrochloride Crystalline Form I treatment groups (200 and 50 mg/kg). Drugs were administered by oral gavage once daily; dosing frequency depended on the individual case for tumor growth. Tumor volume [tumor volume (V)=tumor size (L)×short diameter of tumor (S)$^2$/2] was measured using calipers once every 3 days. The animals were sacrificed 24-hour after the last drug administration and weighed. The tumor was removed and weighed to accurately calculate the tumor size. All group data was analyzed using the t test. If the p value was <0.05, it was considered to be statistically significant.

Efficacy determination: tumor inhibition rate=[1−treatment group mean tumor weight (T)/control group mean tumor weight (C)]×100%

The results showed that Icotinib hydrochloride Crystalline Form I given orally in the A431 xenograft mouse model had significant anti-tumor effects and a dose-response relationship. Efficacy results between Icotinib hydrochloride Crystalline Form I and erlotinib were comparable at 200 mg/kg, with erlotinib demonstrating modestly better tumor inhibition (77.6%) in this model than Icotinib hydrochloride Crystalline Form I (64.6%). However, toxicity was greater with erlotinib; 3 of 8 animals died after 5 days at 200 mg/kg necessitating a dose reduction to 100 mg/kg after a 9 day recovery period. Icotinib was reduced to 100 mg/kg at this point as well for consistency and comparability. No toxic effects were observed for the Icotinib group at either dose. At the experiment termination, animals in the erlotinib group had lost weight and appeared sluggish in contrast to animals in the Icotinib group that had gained weight and tolerated drug administration for an additional 9 days.

Test 5: Comparison of Icotinib Hydrochloride Crystalline Form I with Iressa™ Tablets on Inhibition of Human Tumor Xenograft Models in Nude Mice Methods: Methodologies described in Test 4 were used in this study to compare the antitumor activities of Icotinib hydrochloride Crystalline Form I and Iressa™ tablets against the H460 human lung adenocarcinoma xenograft.

The results showed that when abrasive powders of Icotinib hydrochloride Crystalline Form I and Iressa™ tablets were administered by oral gavage once daily for 14 days, the H460 tumor inhibition rates of the high, medium and low dose groups (120, 60 and 30 mg/kg) of Icotinib hydrochloride were 52.0, 49.3 and 37.5%; the tumor inhibition rate of the Iressa™ group (120 mg/kg) was 38.3%. The Icotinib hydrochloride Crystalline Form 130 mg/kg group showed the same inhibitory activity against the H460 human tumor xenograft as the 120 mg/kg Iressa™ group while the two higher dose groups demonstrated greater inhibitory activity than the 120 mg/kg Iressa™ dose level. Toxicity appeared greater with Iressa™ than with Icotinib hydrochloride Crystalline Form I, with animals showing reduced body weight and appearing sluggish.

Pharmacology and toxicology experiments in Beagle dogs, mice, and rats using Icotinib hydrochloride Crystalline Form I were also conducted. The results showed that: Icotinib hydrochloride Crystalline Form I had low oral toxicity, no bone marrow toxicity and reversible liver toxicity. Safety pharmacological test results showed that Icotinib hydrochloride Crystalline Form I had no effect on respiration, blood pressure and circulatory function, and no effect on autonomic nervous system activity or the central nervous system. Additional toxicity testing results showed no teratogenic, mutagenic and reproductive toxicity.

In addition, non-clinical pharmacokinetic studies of Icotinib hydrochloride Crystalline Form I in Beagle dogs and rats were conducted. The results showed that Icotinib hydrochloride Crystalline Form I given orally was well absorbed with an absolute bioavailability of 27-62% in rats and dogs. The drug reached peak plasma concentrations (Tmax) in approximately 1 hour and was, eliminated mainly through fecal excretion and with a small portion through urine. Icotinib hydrochloride was widely distributed to various tissues, but was low in brain tissue, indicating the drug does not easily cross the blood-brain barrier. No significant induction effect on P450 enzymes in rat liver was found, and no inhibitory activity on drug metabolism enzymes was found for Icotinib hydrochloride Crystalline Form I.

Test 6: Clinical Trials

1) Using Icotinib hydrochloride Crystalline Form I to prepare tablets, a Phase I clinical safety study was completed on 76 subjects administered single doses of 25, 50, 100, 150, 225, 325, 425, 575 and 1025 mg. The results showed that 25-1025 mg single doses were safe.

2) A Phase IIa clinical trial of PK, safety and efficacy conducted on 104 patients with advanced non-small cell lung cancer (NSCLC) that had failed at least one platinum-based chemotherapy regimen was completed with orally administered Icotinib hydrochloride Crystalline Form I tablets without food. The efficacy evaluation of the treatment is shown in Table 4. Definitions of terms used: PR: partial remission, CR: complete remission, SD: stable disease, PD: progression of disease, ORR: objective response rate, DCR: disease control rate.

TABLE 4

Efficacy evaluation of advanced NSCLC patients after treatment with various doses of Icotinib hydrochloride Crystalline Form I

| Dosing | Enrolled # | CR | PR | SD | PD | ORR | DCR |
|---|---|---|---|---|---|---|---|
| 225 mg/day (75 mg, 3 times a day) | 7 | 0 | 0 | 6 | 1 | 0.00% (0/7) | 85.70% (6/7) |
| 300 mg/day (100 mg, 3 times a day) | 27 | 2 | 5 | 10 | 10 | 25.93% (7/27) | 62.96% (17/27) |
| 375 mg/day (125 mg, 3 times a day) | 24 | 0 | 9 | 13 | 2 | 37.50% (9/24) | 91.70% (22/24) |
| 450 mg/day (150 mg, 3 times a day) | 11 | 0 | 5 | 5 | 1 | 45.45% (5/11) | 90.10% (10/11) |
| 600 mg/day (200 mg, 3 times a day) | 3 | 0 | | 2 | 1 | 0.00% (0/3) | 66.67% (2/3) |
| 300 mg/day (150 mg, Twice a day) | 23 | 1 | 6 | 9 | 4 | 30.43% (7/23) | 69.57% (16/23) |
| 400 mg/day (200 mg, Twice a day) | 9 | 0 | 0 | 5 | 3 | 0.00% (0/9) | 55.56% (5/9) |

The above data demonstrate that Icotinib hydrochloride Crystalline Form I was effective in the treatment of non-small cell lung cancer.

Test 7: Pharmacokinetic Study of the Different Crystalline Forms of Icotinib Hydrochloride and the Free Base Form of Icotinib Drugs and reagents: Icotinib (free base) and Icotinib hydrochloride crystalline forms I, II, III, and IV were ground to fine particles. The material content (purity) was not less than 99.0%. Sodium carboxymethyl cellulose was medical supply graded.

Experimental animals: Wistar rats, male and female, 150-220 g each.

Pharmaceutical preparation: Weigh the appropriate amount of each substance and add sodium carboxymethyl cellulose to 0.5%. Prepare a suspension at a final concentration of 3.5 mg/mL in water.

Administration and sample collection: Each suspension was administered orally to fasted Wistar rats at a dose equivalent to 35 mg/kg Icotinib hydrochloride in a dose volume of 10 ml/kg. Approximately 0.5-1.0 mL of blood was collected in heparinized tubes at time intervals of 1, 2, 3, 6, 10, and 24 minutes after drug administration, centrifuged, and plasma was collected and stored at −20° C.

After purification, samples were analyzed by high performance liquid chromatography. The chromatographic conditions utilized C18-silane bonded silica as stationary phase, 0.02 mol/L of sodium dihydrogen phosphate in acetonitrile (40:60, using sodium hydroxide solution to adjust pH to 5.0) as the mobile phase and a detection wavelength of 334 nm. The area under the concentration-time curve for each compound is shown in the table below.

| | The area under the concentration-time curve (0-t) | The area under the concentration-time curve (0-infinity) |
|---|---|---|
| Crystalline Form I | 91.80 | 93.73 |
| Crystalline Form II | 88.28 | 90.77 |
| Crystalline Form III | 89.23 | 90.26 |
| Crystalline Form IV | 86.29 | 90.23 |
| Free base | 28.83 | 29.36 |

The above experiment showed that the area under the concentration-time curve (O-t) and area under the concentration-time curve (O-infinity) of Icotinib hydrochloride Crystalline Forms I, II, III, and IV were as high as approximately 3 times that of the free base form. Therefore, Icotinib hydrochloride Crystalline Forms I, II, III, and IV have significantly better relative bioavailability than the free base of Icotinib.

We claim:

1. A compound of Formula I, wherein the compound is the hydrochloride salt of 4-[(3-ethynyl-phenyl)amino]-6,7-benzo-12-crown-quinazoline in a crystalline form

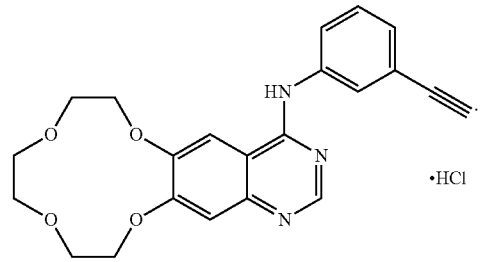

Formula I

2. A method for preparing the compound of claim 1, comprising the following steps:

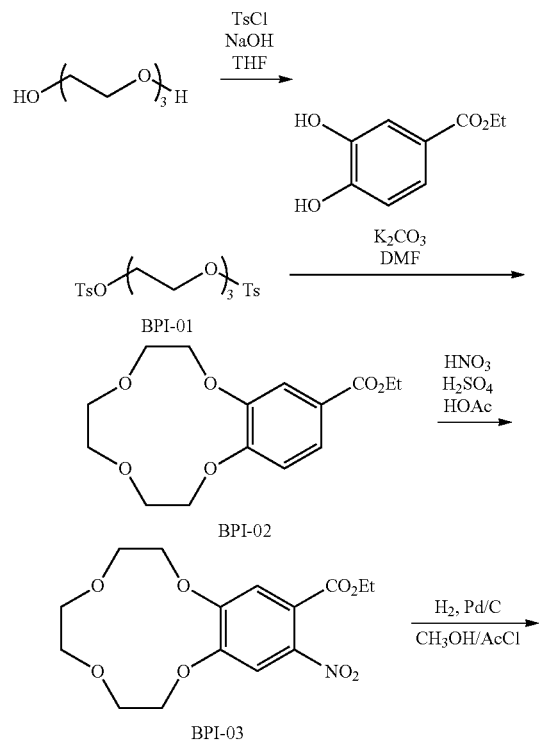

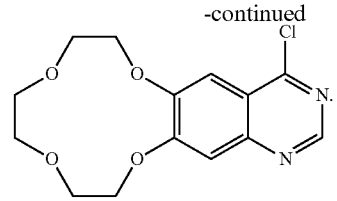

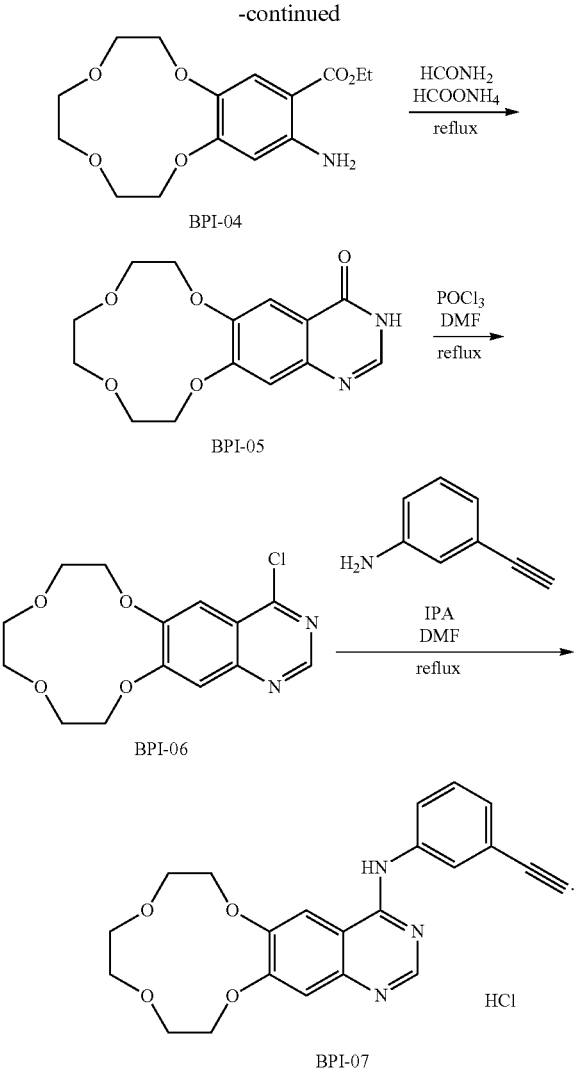

3. Compounds of following formulae:

4. Crystalline Form I of 4-[(3-ethynyl-phenyl)amino]-6,7-benzo-12-crown-quinazoline hydrochloride salt, which is characterized by the following angle diffraction peaks in X-ray powder diffraction pattern:

| Peak # | Diffraction angle (2θ°) | Spacing | Relative intensity |
|---|---|---|---|
| 1 | 5.740 | 15.3841 | 100 |
| 2 | 10.720 | 8.2459 | 13 |
| 3 | 11.500 | 7.6884 | 10 |
| 4 | 21.400 | 4.1487 | 17 |
| 5 | 22.980 | 3.8669 | 12 |

5. Crystalline Form II of 4-[(3-ethynyl-phenyl)amino]-6,7-benzo-12-crown-quinazoline hydrochloride salt, which is characterized by the following angle diffraction peaks in X-ray powder diffraction pattern:

| Peak # | Diffraction angle (2θ°) | Spacing | Relative intensity |
|---|---|---|---|
| 1 | 7.460 | 11.8405 | 46 |
| 2 | 15.040 | 5.8857 | 30 |
| 3 | 16.240 | 5.4534 | 31 |
| 4 | 22.460 | 3.9553 | 100 |
| 5 | 22.840 | 3.8903 | 47 |

6. Crystalline Form III of 4-[(3-ethynyl-phenyl)amino]-6,7-benzo-12-crown-quinazoline hydrochloride salt, which is characterized by the following angle diffraction peaks in X-ray powder diffraction pattern:

| Peak # | Diffraction angle (2θ°) | Spacing | Relative intensity |
|---|---|---|---|
| 1 | 9.720 | 9.0919 | 100 |
| 2 | 10.400 | 8.4989 | 53 |

7. Crystalline Form IV of 4-[(3-ethynyl-phenyl)amino]-6,7-benzo-12-crown-quinazoline hydrochloride salt, which is characterized by the following angle diffraction peaks in X-ray powder diffraction pattern:

| Peak # | Diffraction angle (2θ°) | Spacing | Relative intensity |
|---|---|---|---|
| 1 | 6.340 | 13.9295 | 84 |
| 2 | 7.660 | 11.5318 | 100 |
| 3 | 12.260 | 7.2134 | 34 |
| 4 | 15.700 | 5.6398 | 36 |
| 5 | 16.660 | 5.3169 | 46 |
| 6 | 23.180 | 3.8340 | 74 |
| 7 | 24.980 | 3.5617 | 34 |

8. A method for preparing a Crystalline Form of 4-[(3-ethynyl-phenyl)amino]-6,7-benzo-12-crown-quinazoline hydrochloride salt, comprising dissolution of 4-[(3-ethynyl-phenyl)amino]-6,7-benzo-12-crown-quinazoline hydrochloride salt in a solvent or solvent mixture at reflux, filtration, cooling, crystallization, filtration, and drying to obtain the Crystalline Form.

9. The method of claim 8, wherein the solvent is water, a lower alcohol, ketone, ether, ester, halogenated hydrocarbon, alkane, halogenated benzene, aliphatic nitrile, or an aromatic solvent.

10. The method of claim 9, wherein the solvent is isopropanol, ethyl acetate, 50% aqueous ethanol, water, N,N-dimethylformamide, methanol, ethanol, acetone or propanol.

11. A pharmaceutical composition comprising a therapeutically effective amount of the compound of claim 1 and/or a Crystalline Form of the compound of claim 1 and a pharmaceutically acceptable carrier.

12. The pharmaceutical composition of claim 11, wherein the pharmaceutical composition is suitable for oral administration.

13. The pharmaceutical composition of claim 11, wherein the pharmaceutical composition is in the form of tablet or capsule.

14. The pharmaceutical composition of claim 13, wherein the unit dosage of the tablet or capsule is 25-1025 mg.

15. The pharmaceutical composition of claim 11, wherein the weight percentage of the compound of claim 1 or the Crystalline Form of the compound of claim 1 in the pharmaceutical composition is 1-99%.

16. A method of treating or preventing excessive non-malignant hyperplasia disease, pancreatitis, kidney disease, cancer, angiogenesis or vascular occurrence-related illness in a patient, or for the mammalian embryo cell transplantation, comprising administering to said patient a therapeutically effective amount of the compound of claim 1 or a crystalline form thereof.

17. The method of claim 16, wherein the excessive non-malignant disease is benign skin hyperplasia or benign prostatic hyperplasia.

18. The method of claim 16, wherein the excessive non-malignant proliferative disease, pancreatitis, kidney disease, cancer, angiogenesis or angiogenesis-related disease is selected from: tumor angiogenesis, chronic inflammatory diseases such as rheumatoid arthritis, atherosclerosis atherosclerosis, skin diseases such as psoriasis, and scleroderma, diabetes-induced skin diseases, diabetic retinopathy, premature retinopathy, age-related degeneration stains, hemangioma, glioma, Kaposi internal tumor, ovarian cancer, breast cancer, lung cancer, pancreatic cancer, lymphoma, prostate, colon and skin tumors and their complications.

19. A method for treating a disease with excessive proliferation of mammalian tissues, comprising administering to a patient with the disease with a therapeutically effective amount of the compound of claim 1 and/or a Crystalline Form of the compound of claim 1.

20. The method of claim 19, further comprising administering to the patient a matrix metalloproteinase inhibitor, a vascular endothelial growth factor receptor kinase inhibitor, an HER2 inhibitor, a vascular endothelial growth factor receptor antibody drug, or an endostatin drug.

21. The method of claim 19, further comprising administering to the patient an anti-tumor agent selected from: mitotic inhibitors, alkylating agents, anti-metabolites, tumor antibiotics, growth factor inhibitors, cell cycle inhibitors, enzymes, enzyme inhibitors, biological response modifiers, and anti-hormones drugs.

22. A method for treating a disease related to tyrosine kinase dysfunction, comprising administering to a patient with the disease with a therapeutically effective amount of the compound of claim 1 and/or a Crystalline Form of the compound of claim 1.

23. The method of claim 22, wherein the disease related to tyrosine kinase dysfunction is selected from the group consisting of brain, lung, liver, bladder, chest, head and neck, esophagus, gastrointestinal tract, breast, ovary, cervix or thyroid tumors and their complications.

24. The method of claim 22, wherein the diseases is selected from the group consisting of brain cancer, lung cancer, kidney cancer, bone cancer, liver cancer, bladder cancer, breast, head and neck cancer, esophageal cancer, stomach, colon, rectum cancer, breast cancer, ovarian cancer, melanoma, skin cancer, adrenal cancer, cervical cancer, lymphoma, or thyroid tumors and their complications.

25. The method of claim 22, wherein the administered dosage of the compound of claim 1 and/or a Crystalline Form of the compound of claim 1 is 50-2,100 mg/day and the administration frequency is 1-3 times a day.

26. The method of claim 25, wherein the administered dosage is 75-1,200 mg/day and the administration frequency is 1-3 times a day.

27. The method of claim 26, wherein the administered dosage is 75-1,200 mg/day and the administration frequency is 2-3 times a day.

28. The method of claim 27, wherein the administered dosage is 100-1,200 mg/day and the administration frequency is 2-3 times a day.

29. The pharmaceutical composition of claim 11, wherein the weight percentage of the compound of claim 1 and/or the Crystalline Form of the compound of claim 1 in the pharmaceutical composition is 1-70%.

30. The pharmaceutical composition of claim 11, wherein the weight percentage of the compound of claim 1 and/or the Crystalline Form of the compound of claim 1 in the pharmaceutical composition is 10-30%.

31. The method of claim 19, wherein the diseases is selected from the group consisting of brain cancer, lung cancer, kidney cancer, bone cancer, liver cancer, bladder cancer, breast, head and neck cancer, esophageal cancer, stomach, colon, rectum cancer, breast cancer, ovarian cancer, melanoma, skin cancer, adrenal cancer, cervical cancer, lymphoma, or thyroid tumors and their complications.

32. The method of claim 19, wherein the administered dosage of the compound of claim 1 and/or the Crystalline Form of the compound of claim 1 is 50-2,100 mg/day and the administration frequency is 1-3 times a day.

33. The method of claim 32, wherein the administered dosage is 75-1,200 mg/day and the administration frequency is 1-3 times a day.

34. The method of claim 33, wherein the administered dosage is 75-1,200 mg/day and the administration frequency is 2-3 times a day.

35. The method of claim 34, wherein the administered dosage is 100-1,200 mg/day and the administration frequency is 2-3 times a day.

* * * * *